(12) United States Patent
Weisenburgh, II et al.

(10) Patent No.: US 7,585,308 B2
(45) Date of Patent: Sep. 8, 2009

(54) HANDLE SYSTEM AND METHOD FOR USE IN ANASTOMOTIC PROCEDURES

(75) Inventors: William B. Weisenburgh, II, Maineville, OH (US); Christopher J. Hess, Cincinnati, OH (US); James W. Voegele, Cincinnati, OH (US); Robert P. Gill, Mason, OH (US); Muta M. Issa, Atlanta, GA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 612 days.

(21) Appl. No.: 11/268,001

(22) Filed: Nov. 7, 2005

(65) Prior Publication Data
US 2006/0224166 A1 Oct. 5, 2006

Related U.S. Application Data

(63) Continuation-in-part of application No. 11/094,606, filed on Mar. 30, 2005, now Pat. No. 7,500,980.

(51) Int. Cl.
*A61B 17/08* (2006.01)
(52) U.S. Cl. ..................................... 606/153
(58) Field of Classification Search .................. 606/153
See application file for complete search history.

(56) References Cited

U.S. PATENT DOCUMENTS

| | | | |
|---|---|---|---|
| 2,137,710 A | 11/1938 | Anderson | |
| 3,108,595 A | 10/1963 | Overment | |
| 4,007,743 A | 2/1977 | Blake | |
| 4,575,371 A * | 3/1986 | Nordqvist et al. | 604/103.07 |
| 4,873,977 A | 10/1989 | Avant et al. | |
| 4,884,572 A | 12/1989 | Bays et al. | |
| 4,911,164 A | 3/1990 | Roth | |
| 4,973,301 A | 11/1990 | Nissenkorn | |
| 5,047,039 A | 9/1991 | Avant et al. | |
| 5,151,105 A | 9/1992 | Kwan-Gett | |
| 5,368,601 A | 11/1994 | Sauer et al. | |
| 5,374,275 A | 12/1994 | Bradley et al. | |
| 5,540,701 A | 7/1996 | Sharkey et al. | |

(Continued)

FOREIGN PATENT DOCUMENTS

WO  WO 2004/000134  12/2003

(Continued)

OTHER PUBLICATIONS

European Search Report, International Application No. PCT/US05/21755, May 21, 2005, pp. 1-4.

(Continued)

*Primary Examiner*—(Jackie) Tan-Uyen T. Ho
*Assistant Examiner*—Gregory A Anderson
(74) *Attorney, Agent, or Firm*—Frost Brown Todd LLC

(57) ABSTRACT

Disclosed is an instrument and method for use in a procedure to effect anastomosis of a patient's bladder and urethra following a prostatectomy. The instrument comprises a tube assembly, and an end effector assembly operably supported thereby, where the end effector assembly includes a positioner assembly and an anchor driver assembly in operable mechanical communication with a handle, for use in performing anastomotic procedures.

2 Claims, 32 Drawing Sheets

U.S. PATENT DOCUMENTS

| | | | |
|---|---|---|---|
| 5,545,171 A | 8/1996 | Sharkey et al. | |
| 5,571,104 A | 11/1996 | Li | |
| 5,591,179 A | 1/1997 | Edelstein | |
| 5,676,670 A | 10/1997 | Kim | |
| 5,690,676 A | 11/1997 | DiPoto et al. | |
| 5,695,504 A | 12/1997 | Gifford, III et al. | |
| 5,707,380 A | 1/1998 | Hinchliffe et al. | |
| 5,749,826 A * | 5/1998 | Faulkner | 600/29 |
| 5,817,113 A | 10/1998 | Gifford, III et al. | |
| 5,836,913 A * | 11/1998 | Orth et al. | 604/107 |
| 5,849,004 A | 12/1998 | Bramlet | |
| 5,868,762 A | 2/1999 | Cragg et al. | |
| 5,954,732 A | 9/1999 | Hart et al. | |
| 5,980,483 A | 11/1999 | Dimitri | |
| 6,022,364 A | 2/2000 | Flumene et al. | |
| 6,024,748 A | 2/2000 | Manzo et al. | |
| 6,074,395 A * | 6/2000 | Trott et al. | 606/104 |
| 6,080,167 A | 6/2000 | Lyell | |
| 6,083,170 A | 7/2000 | Ben-Haim | |
| 6,117,144 A | 9/2000 | Nobles et al. | |
| 6,146,407 A | 11/2000 | Krebs | |
| 6,190,401 B1 | 2/2001 | Green et al. | |
| 6,248,117 B1 | 6/2001 | Blatter | |
| 6,254,570 B1 | 7/2001 | Rutner et al. | |
| 6,264,633 B1 | 7/2001 | Knorig | |
| 6,299,598 B1 | 10/2001 | Bander | |
| 6,391,039 B1 | 5/2002 | Nicholas et al. | |
| 6,440,146 B2 | 8/2002 | Nicholas et al. | |
| 6,461,367 B1 | 10/2002 | Kirsch et al. | |
| 6,508,822 B1 | 1/2003 | Peterson | |
| 6,551,343 B1 | 4/2003 | Tormala et al. | |
| 6,565,579 B2 | 5/2003 | Kirsch et al. | |
| 6,599,311 B1 | 7/2003 | Biggs et al. | |
| 6,666,873 B1 | 12/2003 | Cassell | |
| 6,676,678 B2 | 1/2004 | Gifford, III et al. | |
| 6,695,504 B2 | 2/2004 | Matsumoto | |
| 6,726,697 B2 | 4/2004 | Nicholas et al. | |
| 6,740,098 B2 | 5/2004 | Abrams et al. | |
| 6,743,241 B2 | 6/2004 | Kerr | |
| 6,855,126 B2 | 2/2005 | Flinchbaugh | |
| 6,932,834 B2 | 8/2005 | Lizardi et al. | |
| 6,942,674 B2 | 9/2005 | Belef et al. | |
| 7,094,244 B2 | 8/2006 | Schreck | |
| 7,131,973 B2 | 11/2006 | Hoffman | |
| 7,294,216 B2 | 11/2007 | Whelan | |
| 2002/0049453 A1 | 4/2002 | Nobles et al. | |
| 2002/0177862 A1 | 11/2002 | Aranyi et al. | |
| 2002/0193808 A1 | 12/2002 | Belef et al. | |
| 2003/0032968 A1 | 2/2003 | Kirsch et al. | |
| 2003/0216743 A1 * | 11/2003 | Hoffman | 606/99 |
| 2003/0229364 A1 | 12/2003 | Seiba | |
| 2004/0087995 A1 | 5/2004 | Copa et al. | |
| 2004/0220614 A1 | 11/2004 | Scalzo et al. | |
| 2005/0070938 A1 | 3/2005 | Copa et al. | |
| 2005/0131431 A1 | 6/2005 | Copa et al. | |
| 2005/0228413 A1 | 10/2005 | Binmoeller et al. | |
| 2005/0251167 A1 | 11/2005 | Voegele et al. | |
| 2005/0251168 A1 | 11/2005 | Hess et al. | |
| 2005/0251169 A1 | 11/2005 | Gill et al. | |
| 2005/0251170 A1 | 11/2005 | Weisenburgh, II et al. | |
| 2005/0251171 A1 | 11/2005 | Gill et al. | |
| 2005/0251172 A1 | 11/2005 | Voegele et al. | |
| 2005/0251173 A1 | 11/2005 | Hess et al. | |
| 2005/0251174 A1 | 11/2005 | Gill et al. | |
| 2005/0251175 A1 | 11/2005 | Weisenburgh, II et al. | |
| 2006/0224166 A1 | 10/2006 | Weisenburgh, II et al. | |
| 2006/0224167 A1 | 10/2006 | Weisenburgh, II et al. | |
| 2006/0224168 A1 | 10/2006 | Weisenburgh, II et al. | |
| 2006/0224169 A1 | 10/2006 | Weisenburgh, II et al. | |

FOREIGN PATENT DOCUMENTS

| | | |
|---|---|---|
| WO | WO 2004/000135 | 12/2003 |
| WO | WO 2004/000136 | 12/2003 |
| WO | WO 2004/000137 | 12/2003 |
| WO | WO 2004/098417 | 11/2004 |
| WO | WO 2004/098418 | 11/2004 |
| WO | WO 2006/009998 | 1/2006 |
| WO | WO 2007/056051 | 5/2007 |

OTHER PUBLICATIONS

U.S. Appl. No. 60/582,302, filed Jun. 23, 2004, Gill et al.
U.S. Appl. No. 60/569,195, filed May 7, 2004, Gill et al.
U.S. Appl. No. 60/639,836, filed Dec. 28, 2004, Gill et al.
PCT Search Report for International Application No. PCT/US05/21755 dated Mar. 1, 2006.
PCT Search Report for International Application No. PCT/US06/42786, dated Aug. 24, 2006.

* cited by examiner

HANDLE SYSTEM AND METHOD FOR USE IN ANASTOMOTIC PROCEDURES

RELATED APPLICATIONS

This application is a continuation-in-part of, and where permissible, claims the benefit of the effective filing date of, and incorporates by reference in its entirety, for any and all purposes, the following non-provisional application, and having inventors in common with the instant application: METHOD AND INSTRUMENT FOR EFFECTING ANASTOMOSIS OF RESPECTIVE TISSUES DEFINING TWO BODY LUMENS, Ser. No. 11/094,606, filed Mar. 30, 2005 now U.S. Pat. No. 7,500,980.

FIELD OF THE INVENTION

The present invention relates generally to the anastomosis of two hollow organs, a hollow organ and a vessel or two vessels, and is particularly directed to a method and embodiments of a device that accomplish the same in a minimally invasive manner. More particularly, the present invention also relates to an anastomosis instrument and method that may be used for the anastomosis of the bladder and urethra, especially after a patient's prostate has been removed in a prostatectomy.

BACKGROUND OF THE INVENTION

Prostate cancer is the second most common malignancy in males after cutaneous malignancies and is the second most common cause of cancer death among men in the United States. Prostate cancer is predominantly a disease of elderly men, and the absolute number of cases is expected to increase as worldwide life expectancy increases.

The retropubic approach to prostatectomy as a treatment for prostate cancer was introduced by Millin in 1947. The operation had distinct advantages over perineal prostatectomy in that urologists were more familiar with retropubic anatomy. The retropubic approach to radical prostatectomy also offers the advantage of the ability to perform an extraperitoneal pelvic lymph node dissection for staging purposes. During the past decade, modification in the technique of radical retropubic prostatectomy and the introduction of the anatomic nerve-sparing method resulted in a dramatic decrease in the two morbidities associated with the operation that cause the most concern—incontinence and impotence.

In a radical retropubic prostatectomy, the surgeon removes all or most of the patient's prostate. Because the urethra travels through the prostate, the upper part of the urethra is removed in the surgery. In order to restore proper urinary functions, the bladder and the urethra must be reconnected.

Providing this connection is particularly difficult due to the limited working space and the small size of the urethra. The size of the urethra makes it difficult to accurately place the suture thread through the wall of the urethra. Heretofore, surgeons would execute painstaking suturing operations with tiny, fine needles to reconnect the bladder to the urethra. It has been found that the use of sutures for this purpose has caused certain problems in recovery. These problems include necrosis of the sutured tissues, stricture of the urethra that impedes the flow of fluid through it, and a urethra-bladder connection that is not fluid-tight. In addition, when suturing the urethra to the bladder, the surgeon can possibly inadvertently pierce the nearby neurovascular bundle which can cause incontinence or impotence. The suturing process itself has also been found to be cumbersome, requiring the surgeon to grasp and stretch the bladder and urethra together before making the fine sutures. Sutures may also tear the urethra, resulting in further complications.

With radical retropubic prostatectomies becoming more common, faster and simpler ways to reconnect the bladder and urethra are in demand. It would be further advantageous to provide a means for the anastomosis of the urethra and bladder that does not require the use of potentially damaging sutures.

Additionally, there are other surgical procedures requiring the connection of vessels, hollow organs and tissues defining other body lumens. While some of these structures are large, and more easily manipulated by the surgeon, tissue structures defining other body lumens are smaller and more difficult to manipulate and hold in position while joining ends thereof after, for example, a transectional operation. Accordingly, a faster and simpler way to connect vessels, hollow organs and other tissues defining body lumens would be advantageous.

BRIEF DESCRIPTION OF THE DRAWINGS

The accompanying drawings incorporated in and forming a part of the specification illustrate several aspects of the present invention, and together with the description serve to explain the principles of the invention. In the drawings.

Figure 1:
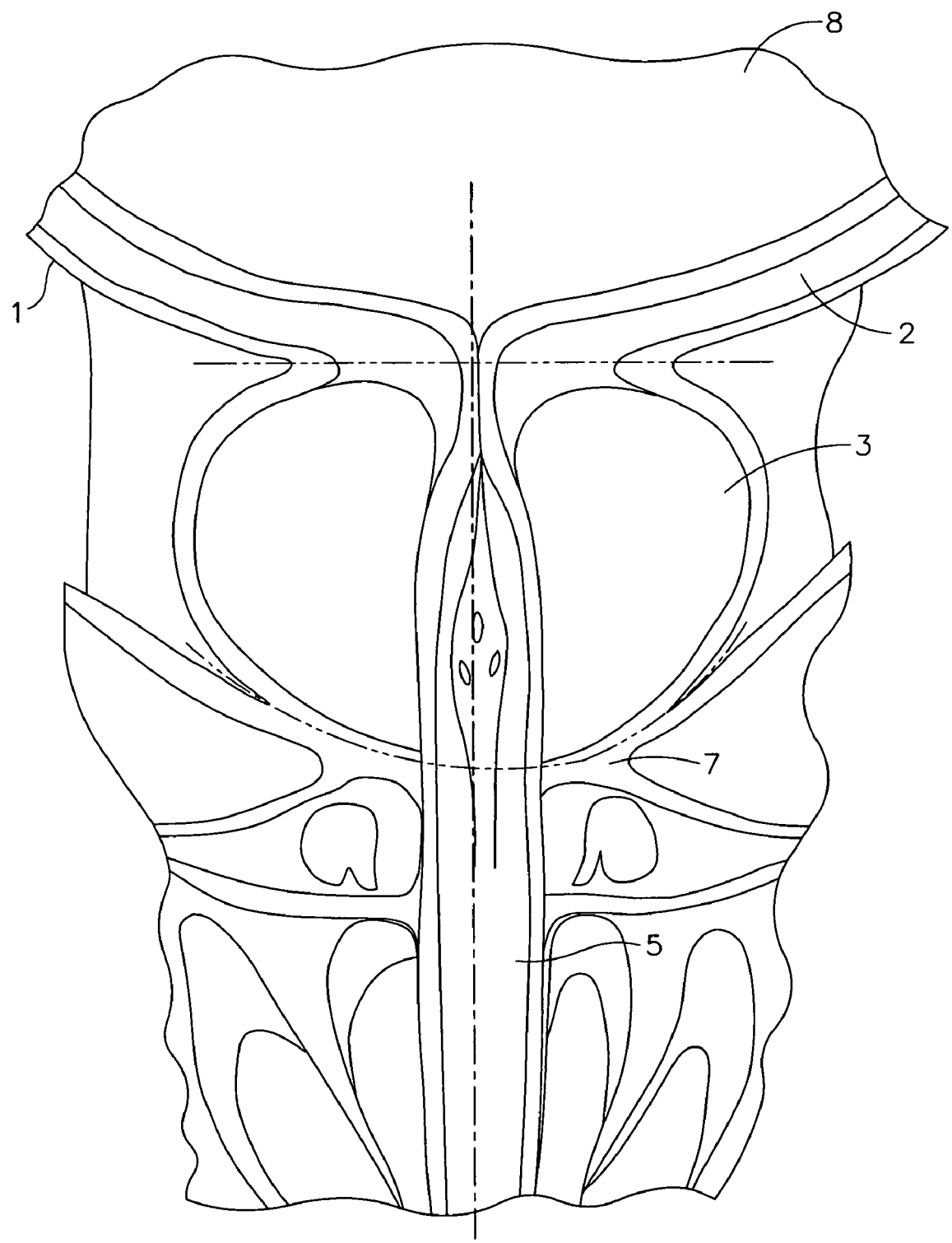
FIG. 1 is a partial, vertical sectional schematic depiction of the positional relationships of the human male bladder, prostate and urethra, and surrounding pelvic floor, prior to a prostatectomy.

Reference will now be made in detail to various alternative embodiments of the method and instrument of the invention, and various alternative components thereof, illustrated in the accompanying drawings.

DETAILED DESCRIPTION OF THE INVENTION

Before the present method and embodiments of an instrument are disclosed and described, it is to be understood that this invention is not limited to the particular process steps, components, and materials disclosed herein as such process steps, components, and materials may vary somewhat. It is also to be understood that the terminology used herein is used for the purpose of describing particular embodiments only and is not intended to be limiting since the scope of the present invention will be limited only by the appended claims.

Unless defined otherwise, all technical and scientific terms used herein have the same meaning as commonly understood to one of ordinary skill in the art to which this invention belongs. Although any method, instrument and materials similar or equivalent to those described herein may be used in the practice or testing of the invention, particular embodiments of a method, instrument and materials are now described.

It must be noted that, as used in this specification and the appended claims, the singular forms "a," "an," and "the" include plural references unless the content clearly dictates otherwise.

In describing and claiming the present invention, the following terminology will be used in accordance with the definitions set out below.

As used herein, the term "anastomosis" means the surgical joining of respective tissues defining body lumens and other hollow body structures, especially the joining of hollow vessels, passageways or organs to create intercommunication between them.

The term "patient," used herein, refers to any human or animal on which an anastomosis may be performed.

As used herein, the term "biocompatible" includes any material that is compatible with the living tissues and system(s) of a patient by not being substantially toxic or injurious and not causing immunological rejection. "Biocompatibility" includes the tendency of a material to be biocompatible.

As used herein, the term "bioabsorbable" includes the ability of a material to be dissolved and/or degraded, and absorbed, by the body.

As used herein, the term "shape memory" includes the tendency of a material, such as but not limited to a suitably prepared nickel-titanium alloy ("nitinol"), to return to a pre-formed shape, following deformation from such shape.

As used herein, the term "integral" means that two or more parts so described are affixed, fastened or joined together so as to move or function together as a substantially unitary part. "Integral" includes, but is not limited to, parts that are continuous in the sense that they are formed from the same continuous material, but also includes discontinuous parts that are joined, fastened or affixed together by any means so as to become substantially immovably affixed to, and substantially unitary with, each other.

As used herein, the term "proximal" (or any form thereof), with respect to a component of an instrument, means that portion of the component that is generally nearest the surgeon, or nearest to the end of the instrument handled by the surgeon, when in use; and with respect to a direction of travel of a component of an instrument, means toward the end of the instrument generally nearest the surgeon, or handled by the surgeon, when in use.

As used herein, the term "distal" (or any form thereof), with respect to a component of an instrument, means that portion of the component that is generally farthest from the surgeon, or farthest from the end of the instrument handled by the surgeon, when in use; and with respect to a direction of travel of a component of an instrument, means away from the end of the instrument generally nearest the surgeon, or handled by the surgeon, when in use.

As used herein, the term "transverse" (or any form thereof), with respect to an axis, means extending in a line, plane or direction that is across such axis, i.e., not collinear or parallel therewith. "Transverse" as used herein is not to be limited to "perpendicular".

As used herein, the term "longitudinal axis", with respect to an instrument, means the exact or approximate central axis defined by said instrument along its greater dimension, i.e., along its length, from its distal end to its proximal end, and vice versa, and is not intended to be limited to imply a straight line, wherein, for example, an instrument includes a bend angle as described herein, it is intended that "longitudinal axis" as used herein follows such bend angle. Where used in association with an end effector, the term "longitudinal axis" means the exact or approximate central axis defined by said end effector extending along its greater dimension, i.e., along its length, from its distal end to its proximal end, and vice versa.

The method and instrument of the present invention utilizes a simple, effective mechanical arrangement for performing anastomosis of respective tissues defining two body lumens, for example, connecting the bladder to the urethra following a prostatectomy. By eliminating more painstaking, cumbersome suturing techniques, anastomosis techniques are improved. For use in the disclosed procedure, there are provided various embodiments of an improved instrument for bringing bladder wall tissues into contact with the pelvic floor tissues, with the openings in the bladder and urethra aligned, and for securing them in position so that they may knit and heal together.

By utilizing the disclosed techniques and an instrument of the present invention, the number of steps in the anastomosis procedure may be decreased, decreasing cost and reducing the required time for the procedure. The present invention may also eliminate complications associated with other anastomosis techniques that require hand suturing.

The present invention provides for a system that allows for, for example, connecting the bladder to the urethra using an instrument inserted through the urethra and into the bladder (in retrograde direction) without the need for access inside the bladder for manipulation and actuation of the instrument. Alternatively, the system and instrument may be configured such that it may be inserted into the bladder and then the urethra in an antegrade direction through small incisions in the patient's abdomen and an upper surface of the bladder. Again, manipulation and actuation of the instrument may be performed by the surgeon from outside the patient's body.

Referring now to the drawings in detail, wherein like numerals indicate the same elements throughout the views, FIG. 1 schematically illustrates in vertical cross section the positioning of a human male bladder 1, bladder wall 2, prostate 3, pelvic floor 7 and urethra 5, prior to a prostatectomy. In a radical prostatectomy, the prostate 3, a lower portion of the bladder wall 2, and an upper portion of the urethra 5 are excised, removing the fluid connection between the bladder lumen 8 and the remaining portion of the urethra. The substantially horizontal broken lines in FIG. 1 schematically illustrate the lines along which the prostate and adjacent bladder and urethra tissues are excised.

Figure 2:
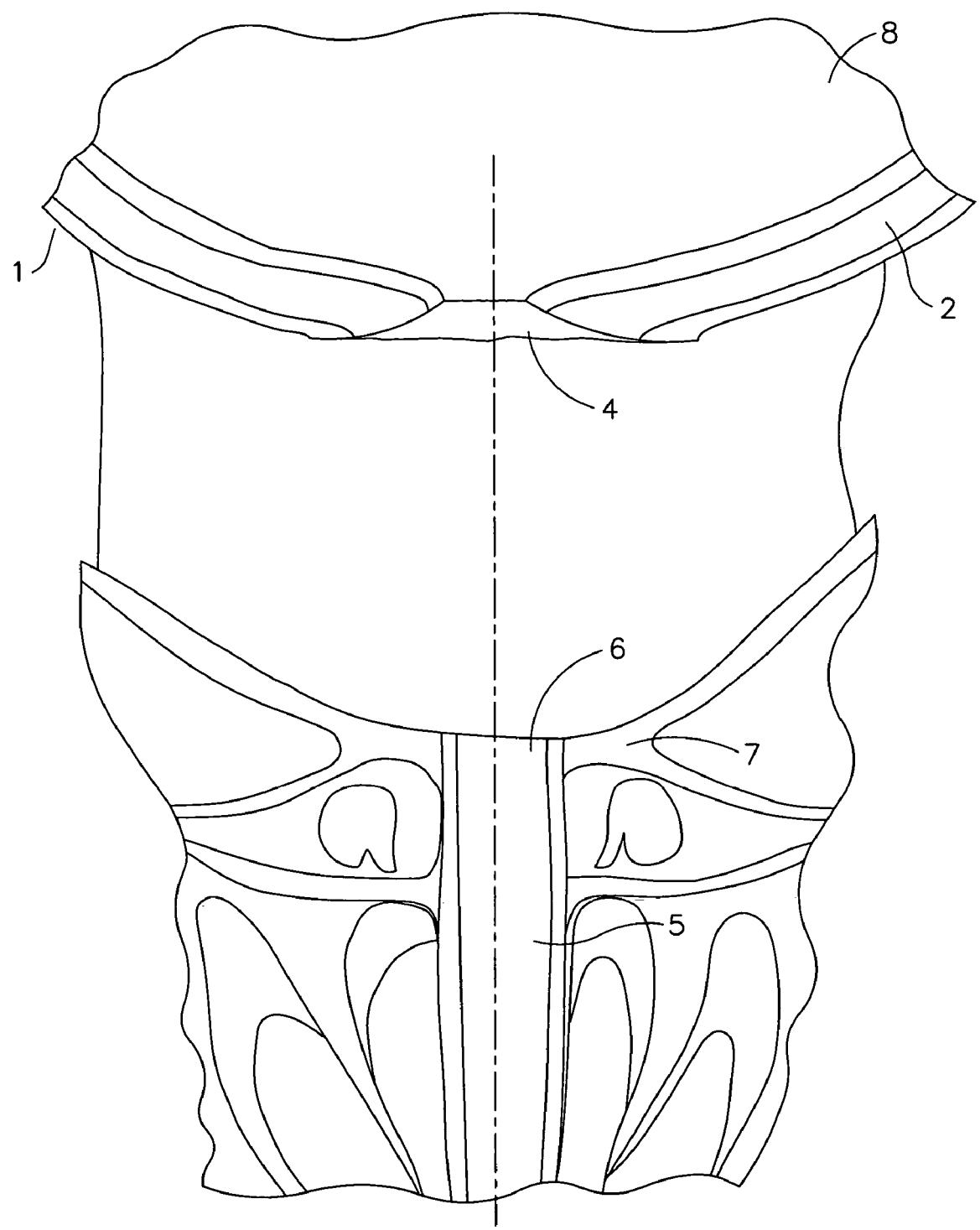
FIG. 2 is a partial, vertical sectional schematic depiction of the positional relationships of the human male bladder and urethra, and surrounding pelvic floor, following a prostatectomy.

FIG. 2 schematically depicts a cross-section of the abdominal cavity following a radical prostatectomy wherein the excision of a portion of the bladder wall 2 results in a bladder opening 4 and the excision of the prostate results in a urethra opening 6 in urethra 5. Following this surgery, bladder opening 4 is typically reduced in size by means known in the art, such as a "tennis racket" suture technique.

Guided Anchor/Balloon Harness Embodiment

Figure 3:
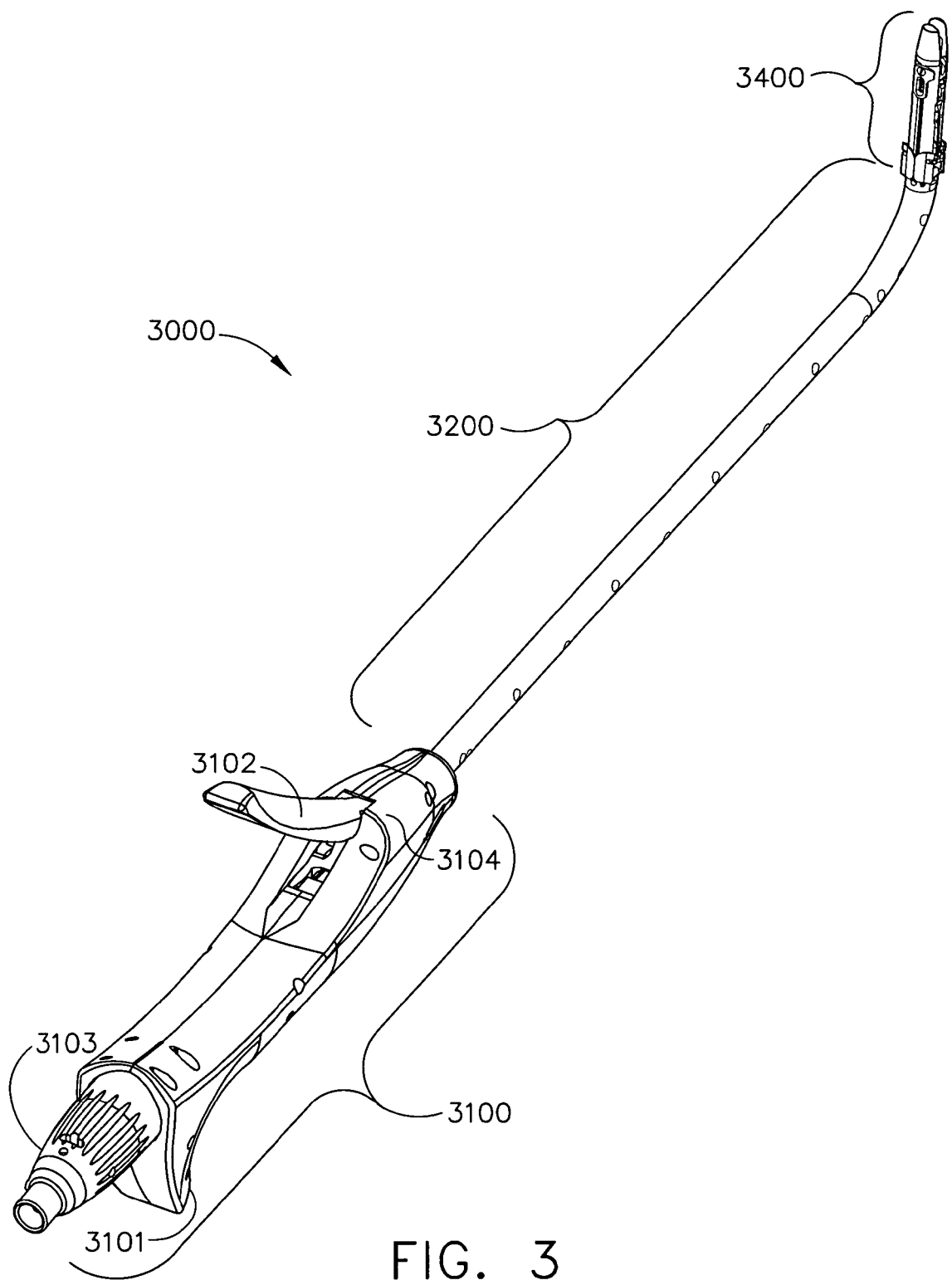
FIG. 3 is a perspective view of an exemplary version of an instrument within the scope of the present invention, including a handle assembly, a tube assembly and an end effector assembly.

FIG. 3 depicts an exemplary embodiment of an instrument 3000 of the present invention, adapted for use in effecting the anastomosis of the bladder and urethra tissues following a radical prostatectomy in accordance with a method of the present invention. The instrument may comprise a handle assembly 3100, a tube assembly 3200 and an end effector assembly 3400. End effector assembly 3400 is adapted to facilitate retrograde insertion into and through a patient's urethra 5 and into the bladder lumen 8 through bladder opening 4 (see FIG. 2). It will be understood by those skilled in the art that instrument 3000 can, alternatively, be designed and configured in an embodiment to be effective to perform steps substantially similar to those herein described via insertion from an antegrade direction, i.e., through incisions through the abdomen and an upper surface of the bladder (not shown), and downwardly through the bladder opening 4 and into urethra opening 6. An example of an instrument so configured is depicted and described in pending U.S. application Ser. No. 11/094,606.

Figure 15:
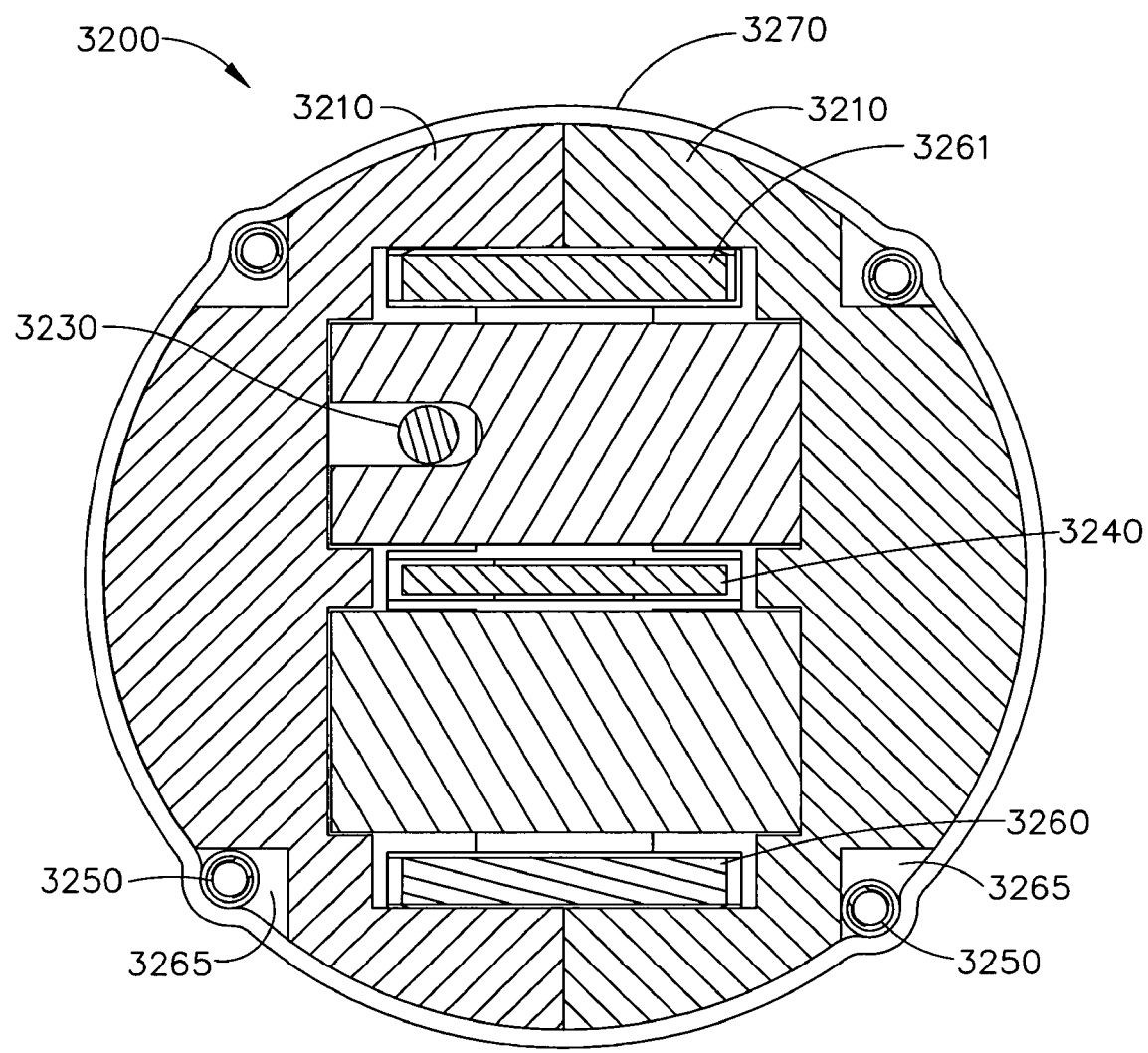
FIG. 15 is an axial cross-sectional view of an exemplary version of a tube assembly having actuating rods or bands disposed therein taken along line 21-21 shown in FIG. 10.

FIGS. 3A-10A are longitudinal cross-sectional views of end effector assembly 3400, and perspective views associated therewith (FIGS. 4A, 5A, 7A, 8A, 9A, and 10A), after insertion into and through the patient's urethra 5 and into the bladder opening 4 in various positions involved in its use. It can be seen that end effector assembly 3400 may comprise body 3401, distal end shield assembly 3410, balloon harness 3430 having harness tip 3434, anchor driver assembly 3460, and positioner assembly 3440. Balloon harness 3430 may be formed of a flexible polymeric material, or any suitable biocompatible material, and may be folded or compressed within distal end shield assembly 3410, with tails 3433 held by harness hooks 760 of anchors 700 as illustrated. End effector assembly 3400 and the assemblies it comprises may be operably connected to, and controlled by, handle assembly 3100 (shown in FIG. 3), via movable members, such as bands, rods, and/or tubes, within tube assembly 3200. Referring to FIG. 15, tube assembly 3200 may comprise a two-piece spine member 3210, guide wire 3230, positioner rod or band 3240, driver opening rod or band 3260, driver actuating rod or band 3261, anchor guide retainer wires 3250 residing in retainer wire channels 3265, and sheath 3270. Spine member 3210 and end effector body 3401 each may be manufactured in two or more pieces, to facilitate manufacture and assembly of the instrument. The pieces of spine member 3210 and end effector body 3401 each may be attached or held together by any suitable means. Referring again to FIG. 15, guide wire 3230 may have a free proximal end and pass through any portion of the length of the instrument, and its distal end may be affixed and made integral with harness tip 3434 (see, e.g., FIG. 4) of balloon harness 3430 by any suitable means.

Referring to FIGS. 3A-10A, and FIG. 15, driver opening rod or band 3260, driver actuating rod or band 3261 and positioner rod or band 3240 may ride longitudinally in proximal and distal directions within channels or tracks within spine member 3210 and end effector body 3401, and may be longitudinally movable with respect to each other, and with respect to spine member 3210 and end effector body 3401.

Rods or bands 3260, 3261 and 3240 may be made of stainless steel, nitinol or any other material having suitable properties of tensile and compressive strength and flexibility, and be optimally sized and shaped, so as to be flexible and be capable of transmitting the pulling and pushing longitudinal forces necessary to actuate the instrument as described herein. Rods or bands 3260, 3261 and 3240 also may be provided with a lubricant on the surfaces thereof to ease their movement, or the channels or tracks in which they ride may be provided with a suitable lubricant. Alternatively, any of rods or bands 3260, 3261 and 3240 may be manufactured of joined materials, such as metal with a polymer sheath, wherein the polymer sheath has low surface friction and/or lubricating properties.

Figure 5:
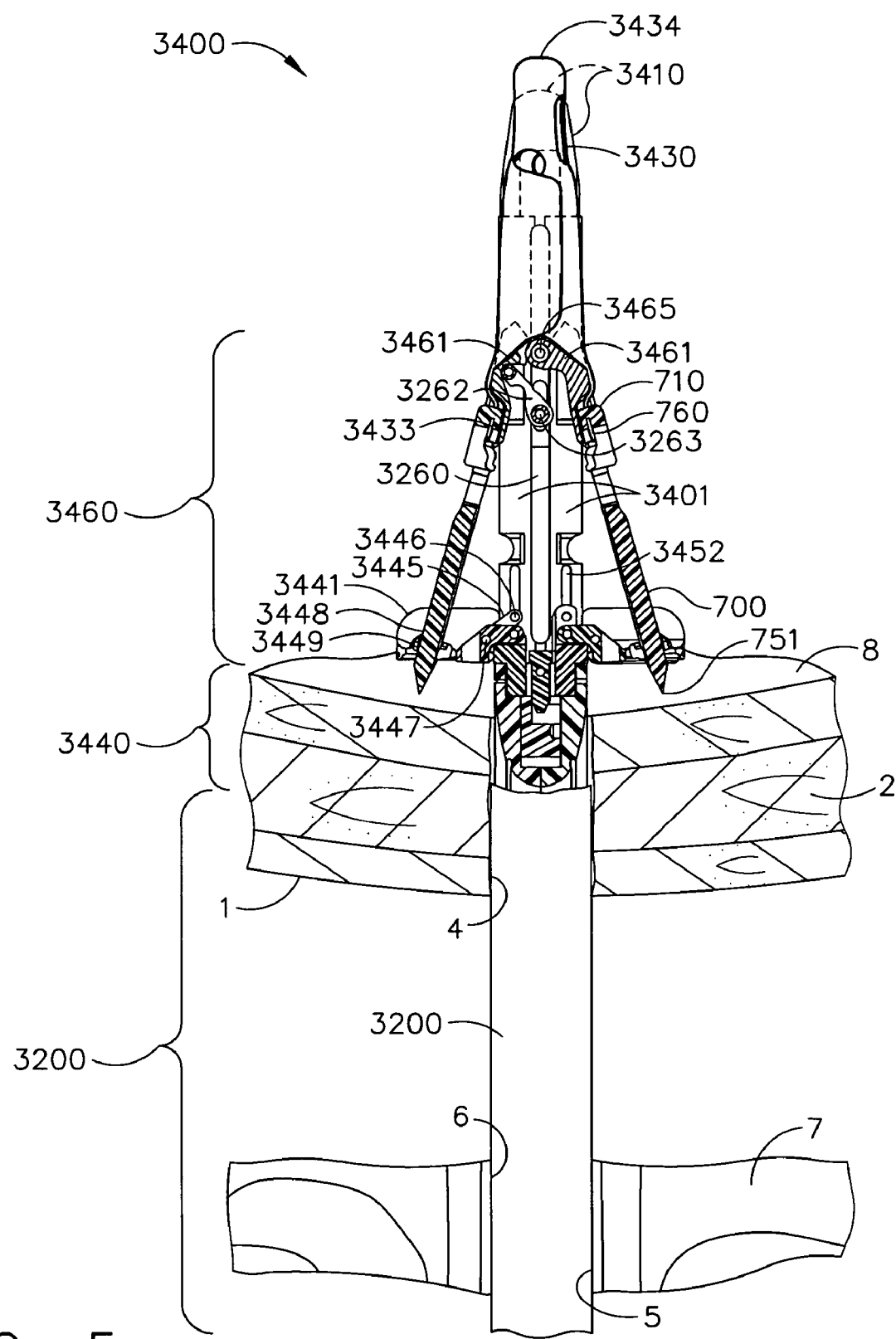
FIG. 5 is a longitudinal cross-sectional view of the end effector assembly shown in FIG. 3, with the positioner arms opened.
Figure 5A:
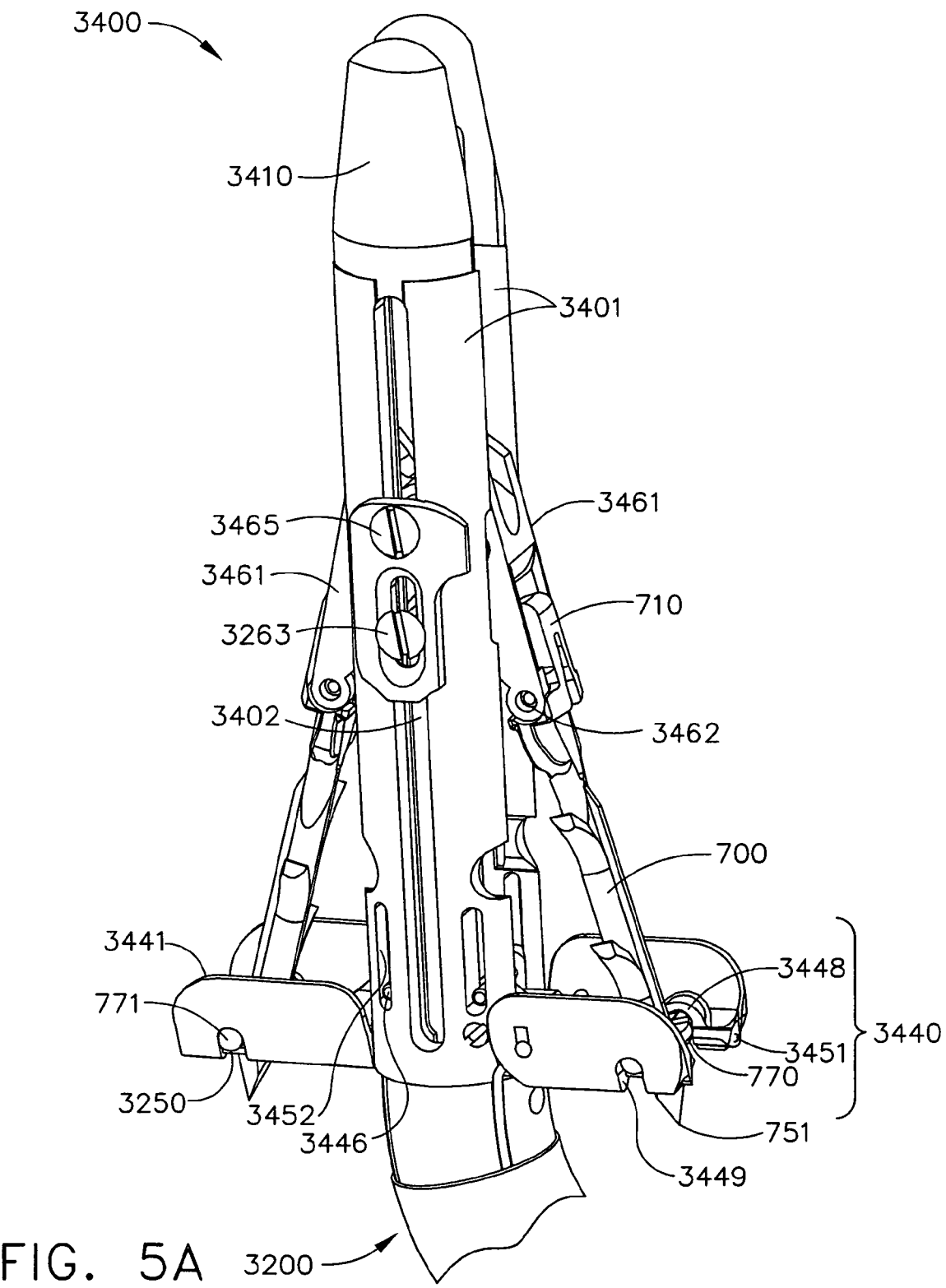
FIG. 5A is a perspective view of the end effector assembly of the instrument shown in FIG. 5.

Body 3401 may be attached and made integral with spine member 3210 by any suitable means. Driver opening rod or band 3260 may be linked at its proximal end to a suitable mechanism controlled by a knob 3103 or other control comprised by handle assembly 3100, and may be linked at its distal end to each of driver arm struts 3262 via driver opening screw pin 3263. Driver actuating rod or band 3261 may be linked at its proximal end to a suitable mechanism controlled by a lever 3102 or other control comprised by handle assembly 3100 and may be linked at its distal end to anchor driver arms 3461 via driver actuating screw pin 3465. Anchor driver arms 3461 may rotate about driver actuating screw pin 3465 to partially extended, fully extended, and retracted positions as shown in the figures, in response to longitudinal movement of driver opening rod or band 3260 acting upon driver arm struts 3262 via driver opening screw pin 3263. Driver actuating screw pins 3465 may ride longitudinally in driver actuation slots 3402 (FIG. 5A) in body 3401. Thus, anchor driver arms 3461 may travel longitudinally, in response to longitudinal movement of driver actuating rod or band 3261 acting upon driver actuating screw pin 3465. Positioner rod or band 3240 may be linked at its proximal end to a suitable mechanism controlled by a knob 3103 or other control comprised by handle assembly 3100 and may be linked at its distal end to positioner struts 3445 via positioner actuating pins 3446 (FIG. 5). Positioner actuating pins 3446 may ride longitudinally in positioner actuation slots 3452 in body 3401. Thus, longitudinal movement of positioner rod or band 3240 (FIG. 15) can effect corresponding longitudinal movement of positioner actuating pins 3446 (FIG. 5), providing the corresponding deployment and retraction of the positioner arms 3441. The other ends of positioner struts 3445 are connected to positioner arms 3441 via positioner strut pins 3447.

Anchor driver arms 3461 may include anchor yokes 3462. (See, for example, FIG. 5A.) Prior to their release as described below, anchors 700 may be rotatably held in anchor yokes 3462 by anchor axle pins 712 (See FIG. 16).

As may be seen in FIGS. 5-7A and 16, prior to the driving of anchors 700, forward ends 751 of anchors 700 may be carried in anchor guides 770. Anchor guides 770 may be rotatably carried in guide yokes 3448 of positioner arms 3441, via anchor guide axle pins 771 that may be carried in guide axle pin notches 3449 in guide yokes 3448. Anchor guide axle pins 771 may be retained in guide axle pin notches 3449 by anchor guide retainer wires 3250. Referring to FIG. 15 and also FIGS. 4-10, anchor guide retainer wires 3250 (see, for example, FIG. 5A) may be situated in channels 3265 in spine member 3210 up to end effector body 3401, and then through retainer wire bores 3451 in positioner arms 3441 and under anchor guide axle pins 771 retained in guide axle pin notches 3449. As will be further explained below, during the procedure described herein anchor guide retainer wires 3250 may be withdrawn from retainer wire bores 3451 so as to release anchor guide axle pins 771 from guide axle pin notches 3449. Anchor guide retainer wires 3250 may be made of nitinol or any other material having suitable properties of tensile strength and flexibility to function effectively as described herein.

The connection and interaction of driver opening rod or band 3260, driver actuating rod or band 3261, and positioner rod or band 3240, to actuate the positioner assembly 3440 and anchor driver assembly 3460, will become apparent in the following description of the use and operation of the described version of the instrument.

Figure 3A:
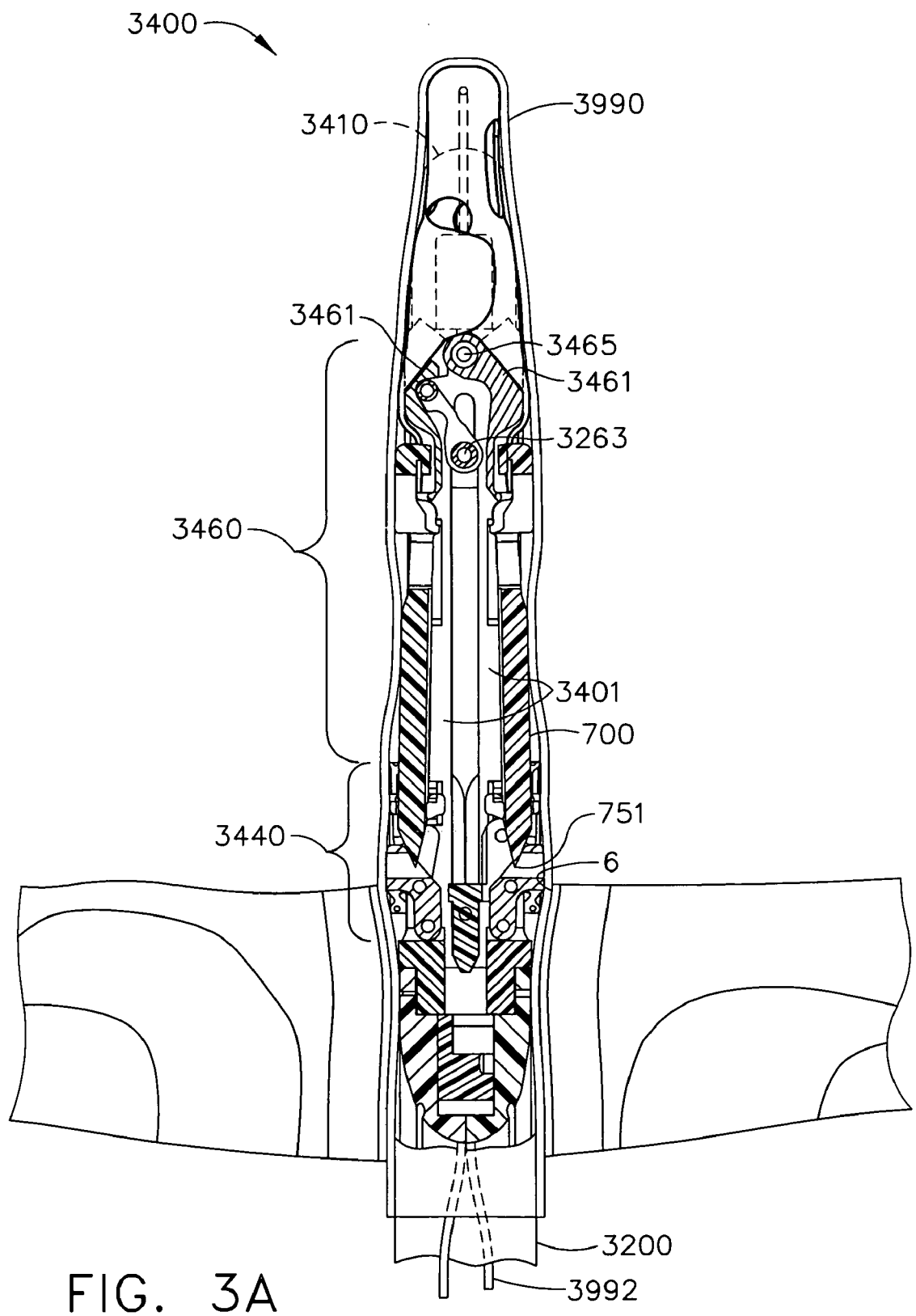
FIG. 3A is a longitudinal cross-sectional view of the end effector assembly of the instrument shown in FIG. 3, shown encased within an end sheath.
Figure 4:
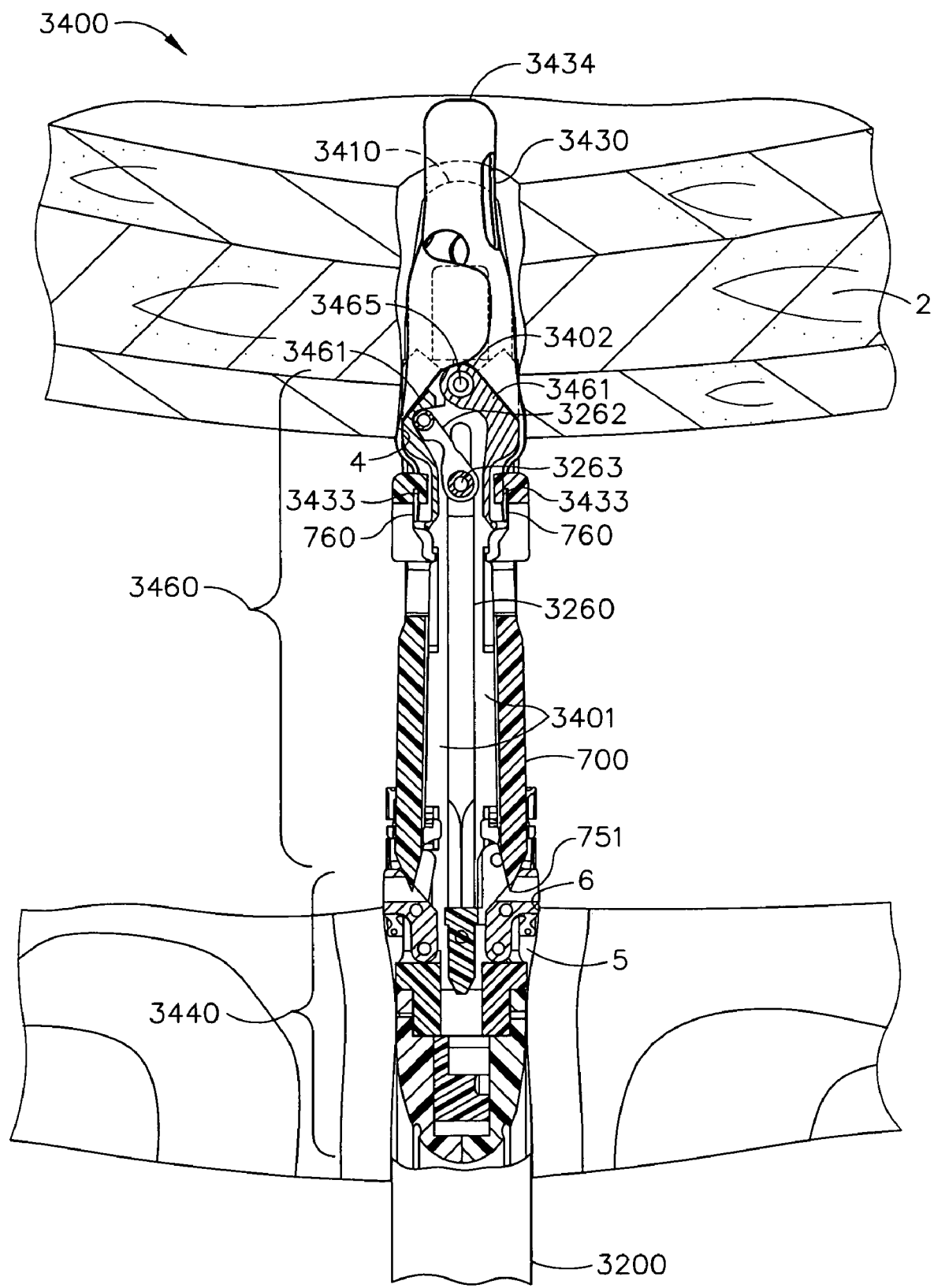
FIG. 4 is a longitudinal cross-sectional view of the end effector assembly of the instrument shown in FIG. 3, shown after insertion into and through a patient's urethra and into the bladder opening.
Figure 4A:
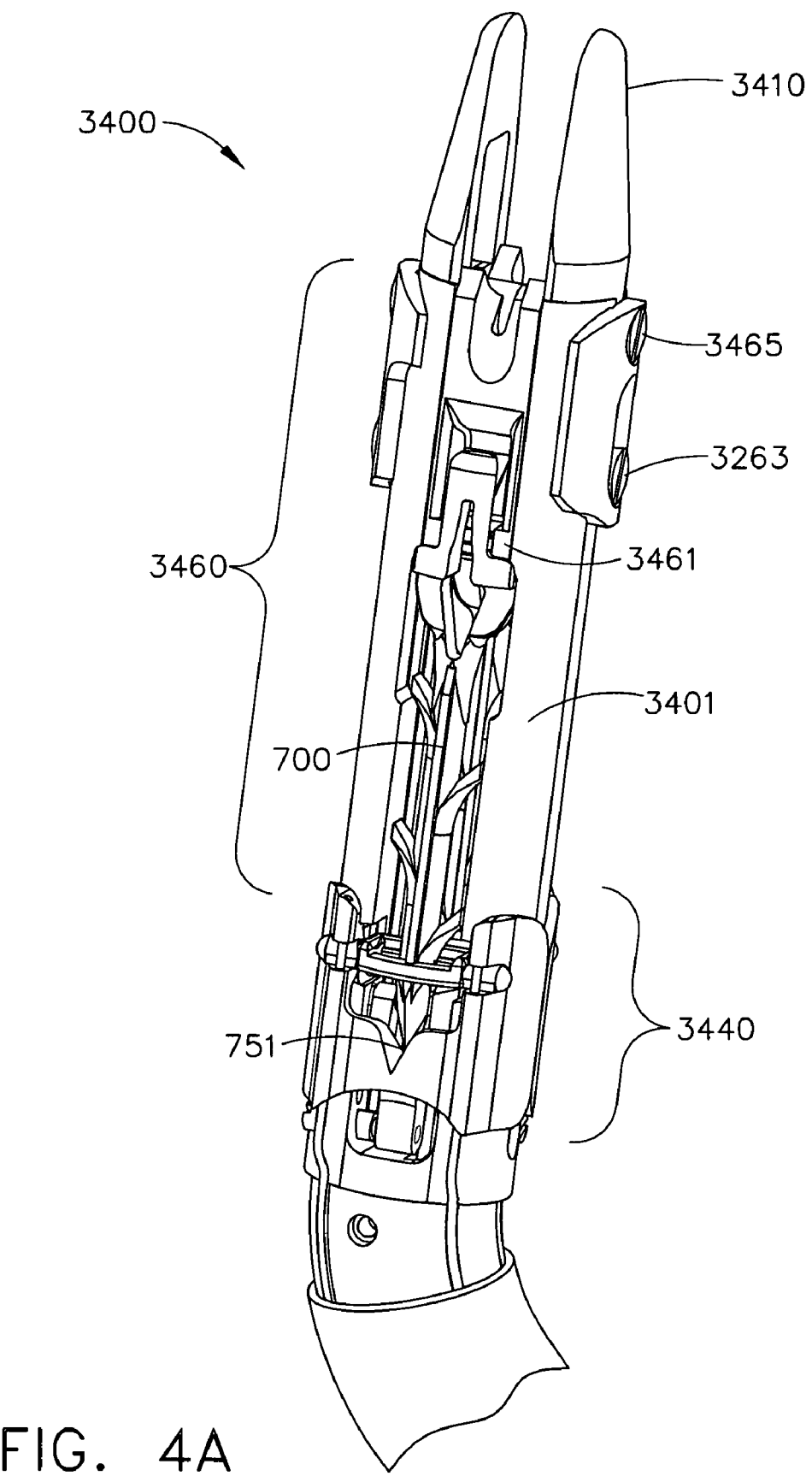
FIG. 4A is a perspective view of the end effector assembly of the instrument shown in FIG. 3.
Figure 24:
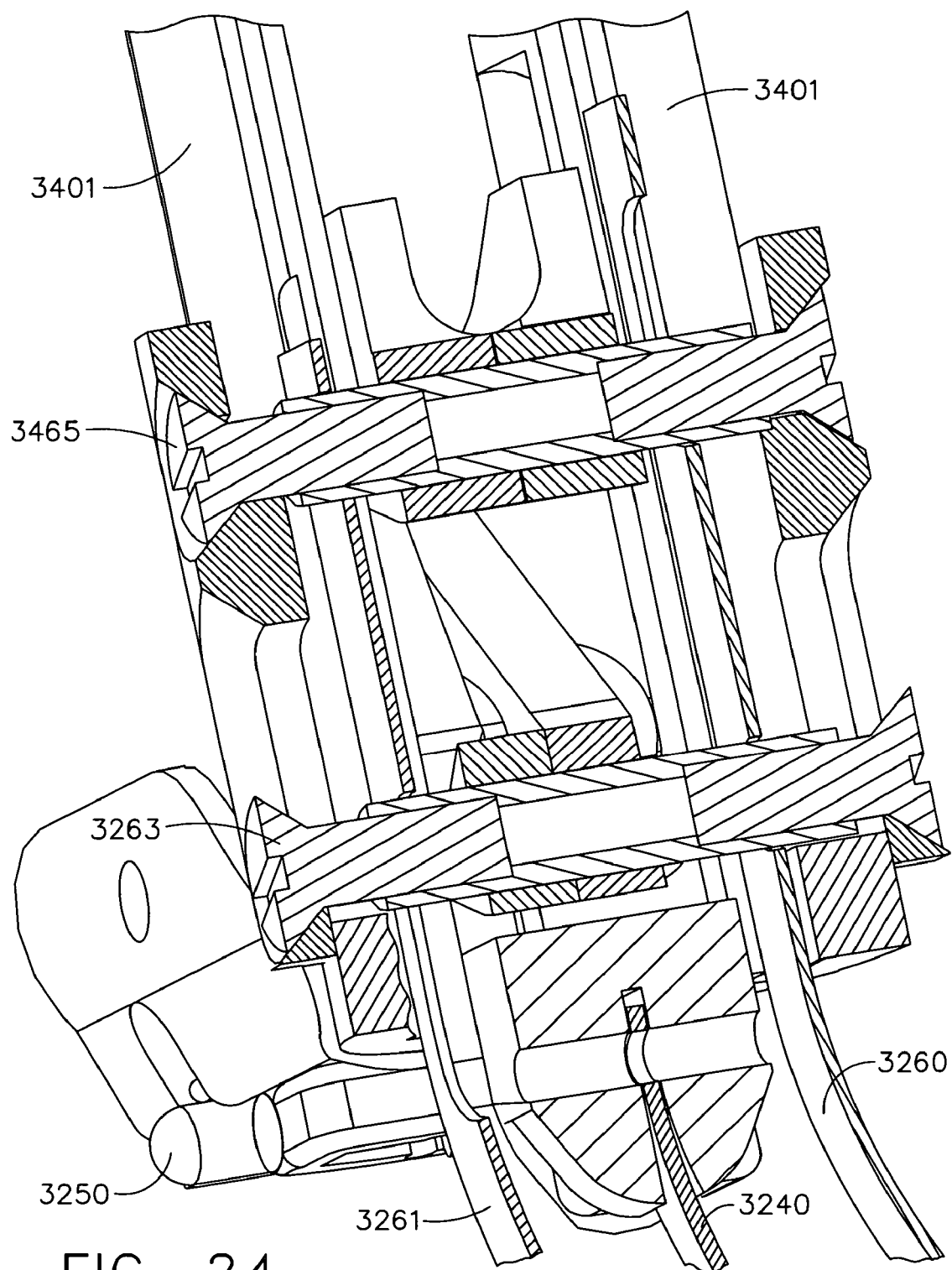
FIG. 24 is a vertical side cross-sectional view of the end effector of FIG. 9A.

As previously noted, and as shown in FIGS. 3A and 5, end effector assembly 3400 may be inserted into and through the patient's urethra 5 in a retrograde direction and into the bladder opening 4, and then into the bladder lumen 8. FIG. 4 depicts an end effector assembly in a pre-deployment position, and FIG. 5 depicts the same end effector assembly after insertion completely into the bladder lumen 8, and after positioner arms 3441 have been opened. From the differences in positions shown FIG. 4 and FIG. 5, it can be seen that proximal movement of positioner actuating pins 3446 (effected by proximal movement of positioner rod or band 3240, see FIG. 24) has caused positioner struts 3445 to push downwardly (relative to the figures) on positioner arms 3441 via positioner strut pins 3447, causing positioner arms 3441 to open outwardly and downwardly, in a manner similar to that of an umbrella opening upside-down. Simultaneously, proximal movement of driver actuating rod or band 3261 (see FIG. 24) acting on driver actuating screw pin 3465 (to which anchor driver arms 3461 are connected) can move anchor driver arms 3461 in a proximal direction, so that forward ends 751 of anchors 700 can remain situated in anchor guides 770. It may be seen in FIG. 5 that the rearward ends 710 of anchors 700 remain closer to the longitudinal axis of the end effector, than the forward ends 751, following the above-described movement. This may be advantageous to minimize the possibility of features of anchors 700 catching or snagging on loose bladder wall tissue during the step of urging the bladder into proximity with the pelvic floor, described below. The movement of positioner rod or band 3240 and driver actuating rod or band 3261 may be effected by any suitable control and mechanism associated with handle assembly 3100, such as by turning knob 3103 to actuate a suitable associated mechanism within handle assembly 3100 (see FIGS. 3 and 15).

Following opening of the positioner arms 3441 to the position shown in FIG. 5, by grasping handle assembly 3100, the surgeon may manipulate the instrument to move the end effector downwardly (with respect to the figures) to bring positioner arms 3441 into contact with bladder wall 2 surrounding bladder opening 4, and subsequently, to urge bladder wall 2 surrounding bladder opening 4 into proximity with pelvic floor 7 surrounding urethra opening 6, with the respective openings of the bladder and urethra substantially aligned, as may be appreciated from FIG. 6.

Figure 6:
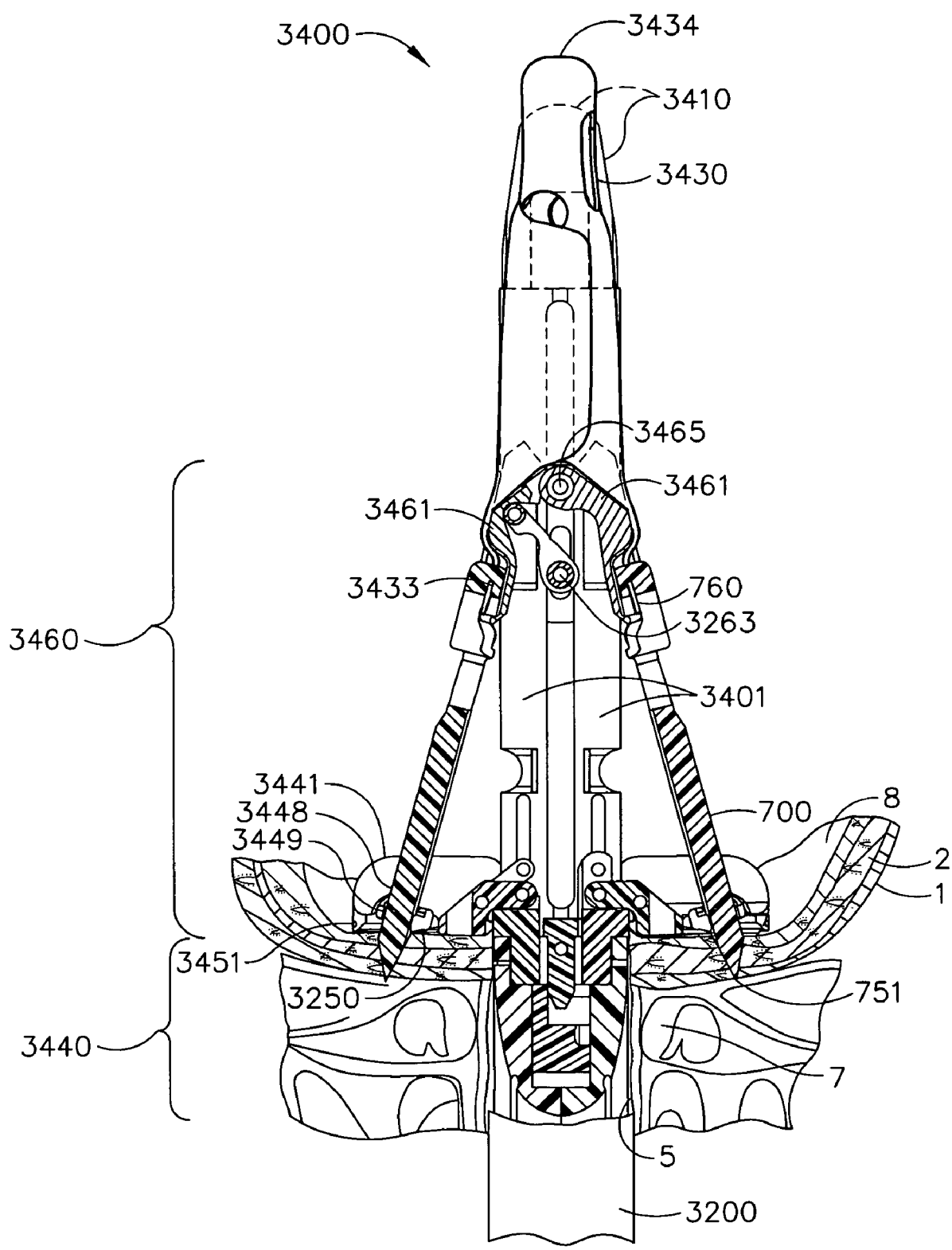
FIG. 6 is a longitudinal cross-sectional view of the end effector assembly shown in FIG. 3, with the positioner arms opened and urging the bladder wall toward the pelvic floor.
Figure 7:
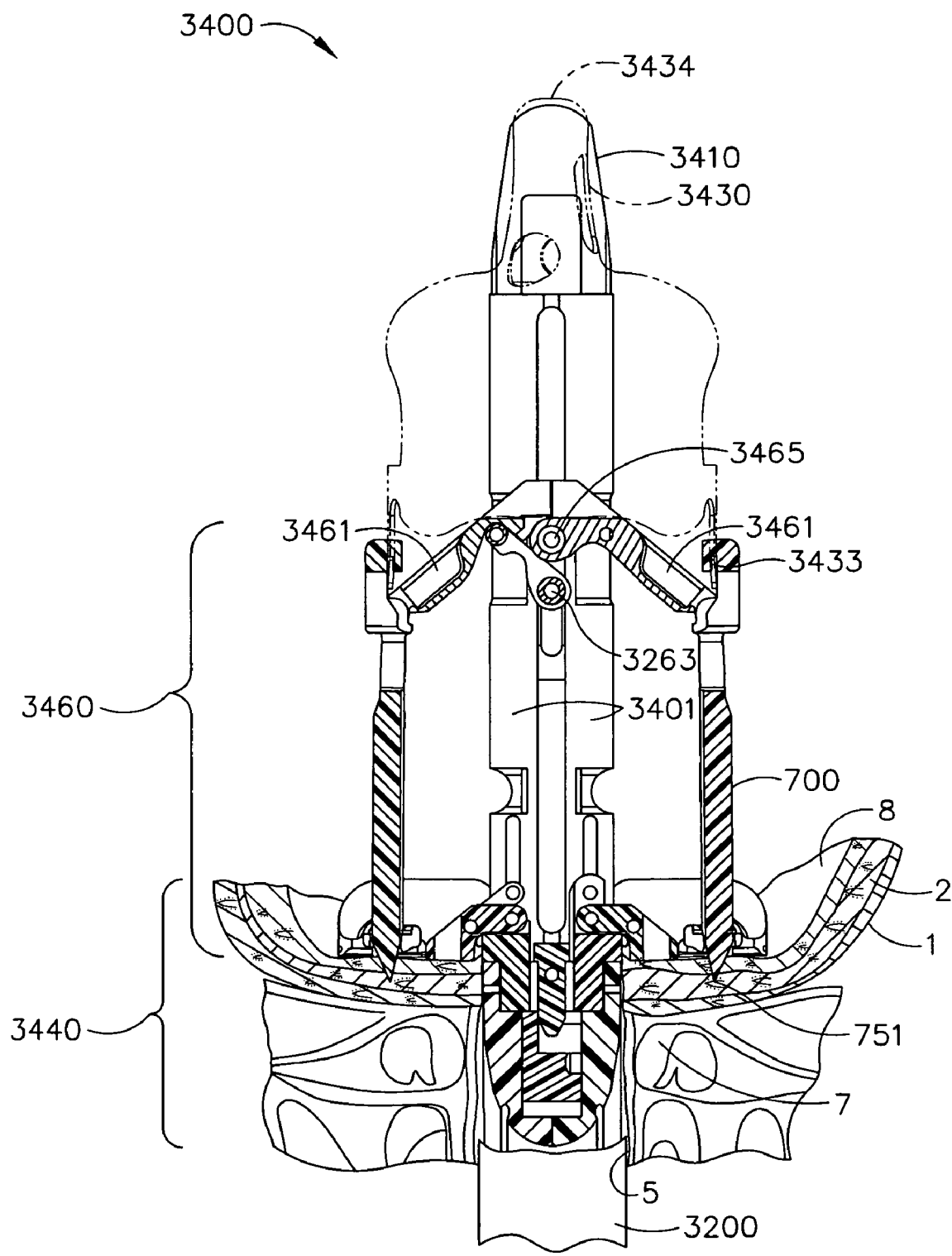
FIG. 7 is a longitudinal cross-sectional view of the end effector assembly shown in FIG. 3, with the positioner arms and driver arms opened and urging the bladder wall toward the pelvic floor
Figure 7A:
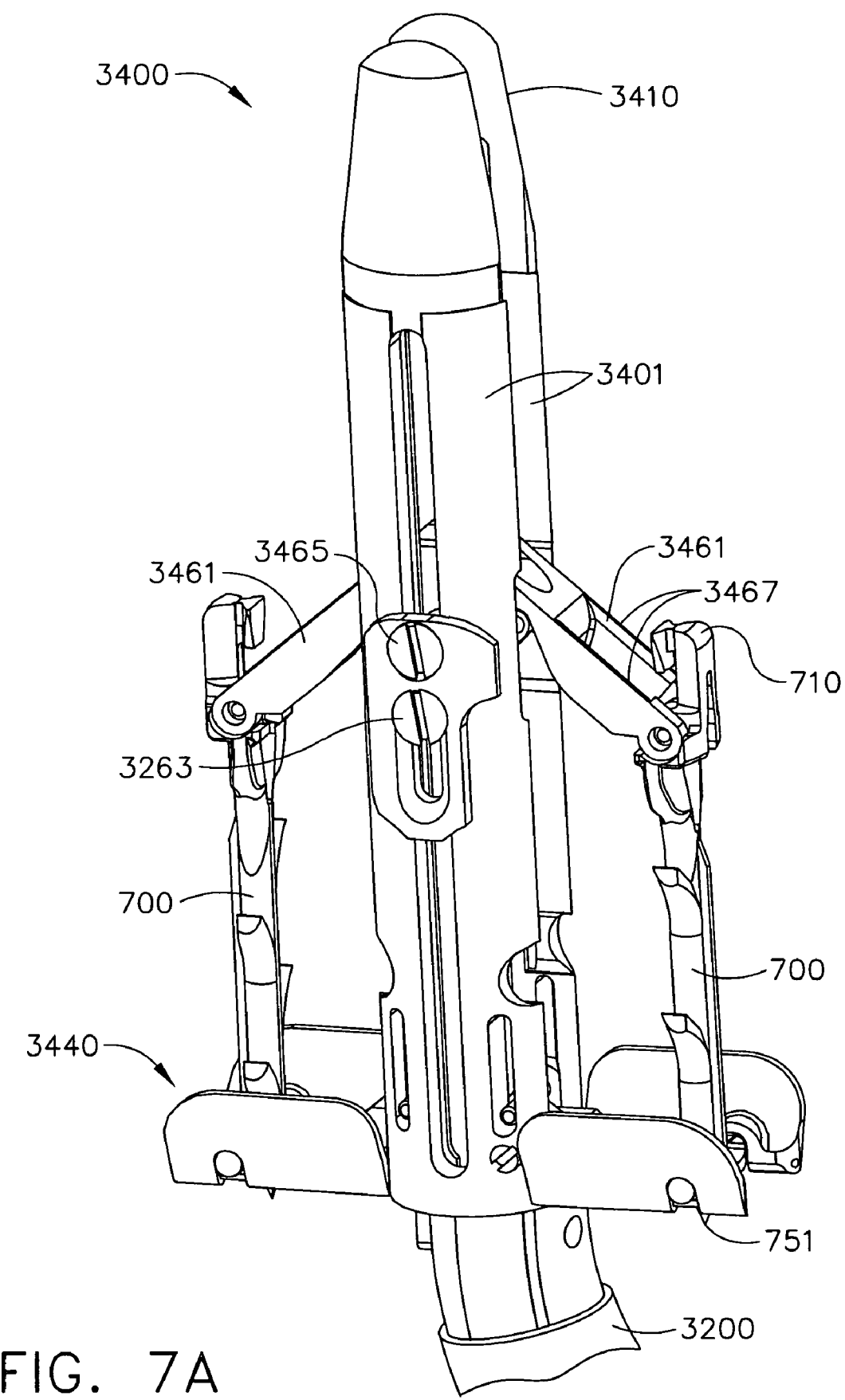
FIG. 7A is a perspective view of the end effector assembly as shown in FIG. 7.

Now referring to and comparing FIGS. 6 and 7, it can been seen that FIG. 7 depicts anchor driver arms 3461 in a fully opened position, bringing anchors 700 into a position closer to parallel or parallel with the longitudinal axis of the end effector, and closer to perpendicular or normal with respect to the pelvic floor. To open anchor driver arms 3461 to the position shown in FIG. 7, driver actuating rod or band 3261 may be held substantially stationary, while driver opening rod or band 3260 may be moved in a distal direction (see FIG. 24). The distal movement of driver opening rod or band 3260 can affect distal movement of driver opening screw pin 3263, which in turn, can cause driver arm struts 3262 to push upwardly and outwardly (relative to the figures) on anchor driver arms 3461 via driver arm strut pins 3264 (not shown). This can move anchor driver arms 3461 outwardly to the position shown in FIG. 7, in a manner similar to that of an umbrella opening. The distal movement of driver opening rod or band 3260 may be effected by any suitable control and mechanism associated with handle assembly 3100, such as by turning or pressing knob 3103 to actuate a suitable associated mechanism within handle assembly 3100 (see FIGS. 3 and 15).

Figure 8:
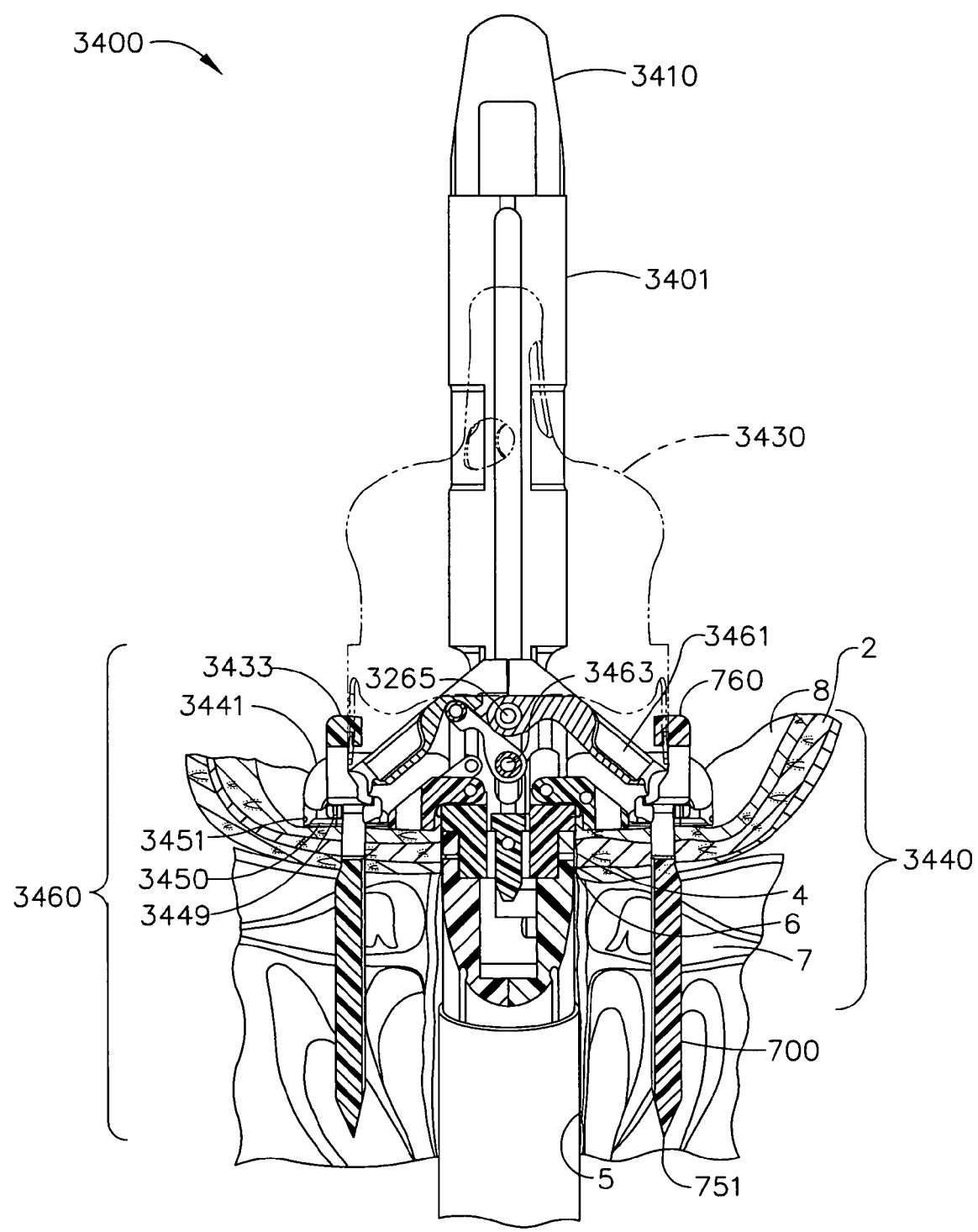
FIG. 8 is a longitudinal cross-sectional view of the end effector assembly shown in FIG. 3, after the driver arms have moved proximally to drive anchors through the bladder wall and into the pelvic floor.
Figure 8A:
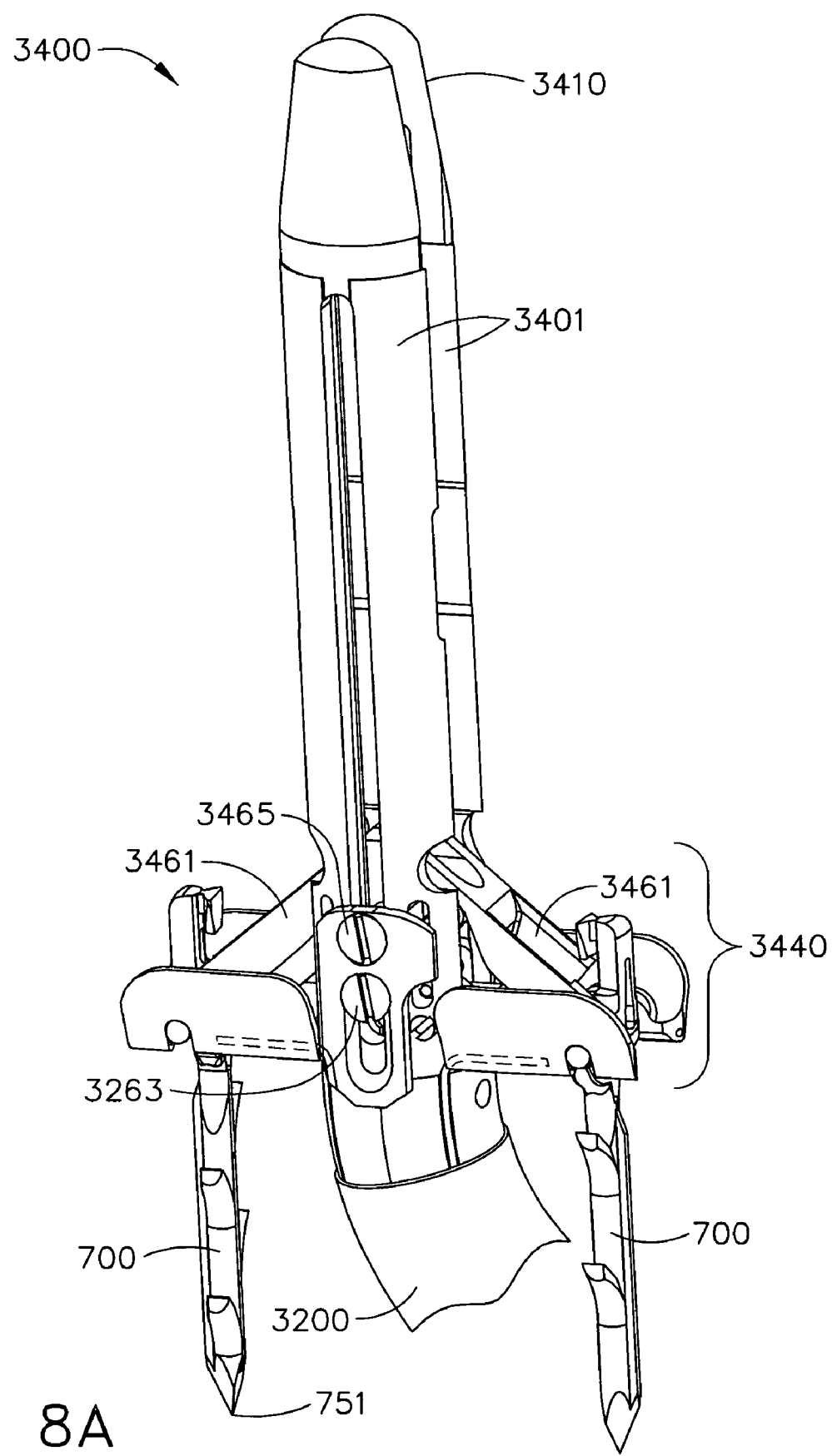
FIG. 8A is a perspective view of the end effector assembly shown in FIG. 8.
Figure 9:
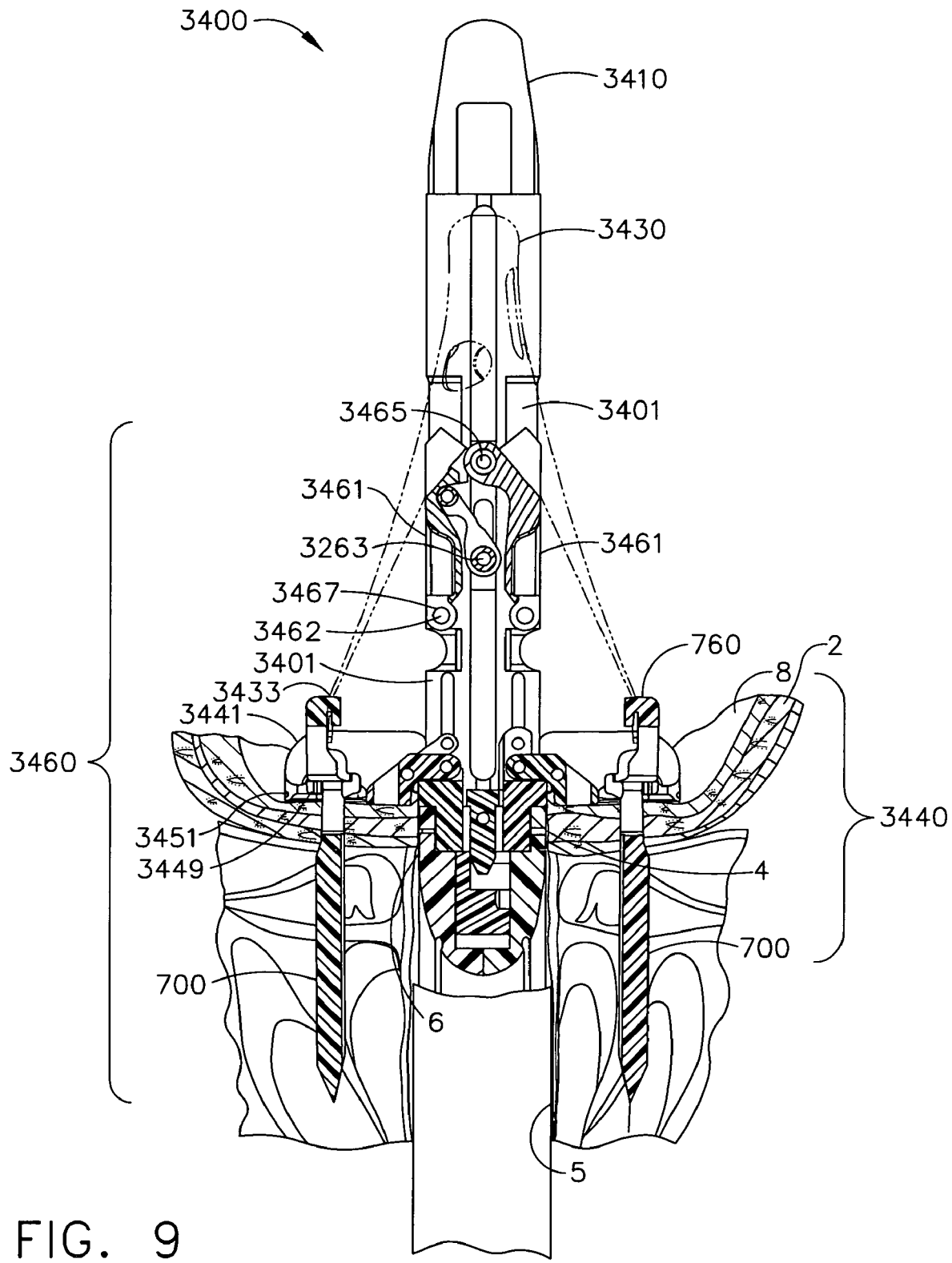
FIG. 9 is a longitudinal cross-sectional view of the end effector assembly shown in FIG. 3, after the anchors have been released from the driver arms and the driver arms have been returned distally to their pre-driving positions and closed.
Figure 9A:
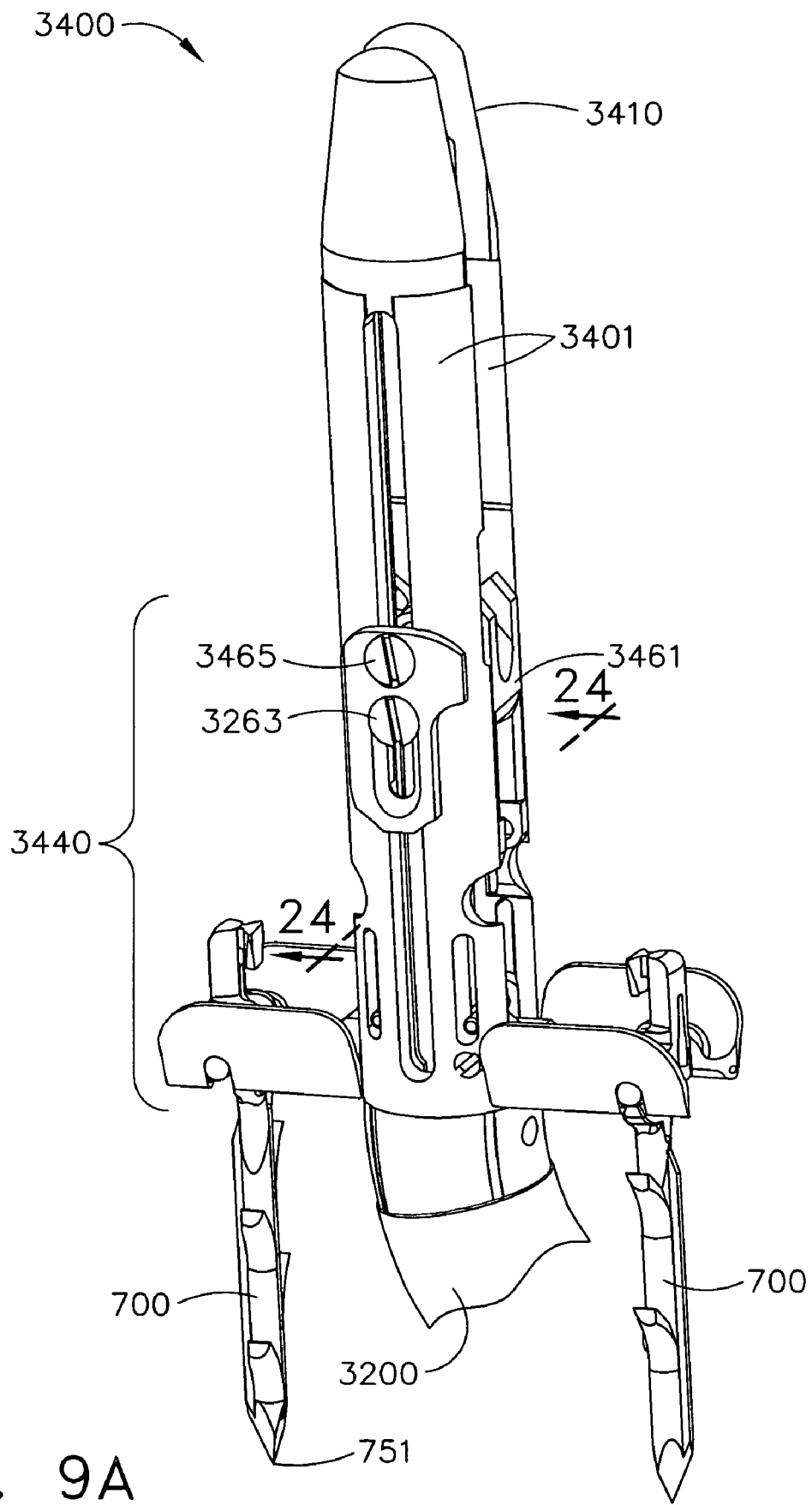
FIG. 9A is a perspective view of the end effector assembly shown in FIG. 9.

Now referring to and comparing FIGS. 7-8A and 24, it can be seen that FIG. 8 depicts the described version of instrument after the opened anchor driver arms 3461 have been moved downwardly (relative to the figures) to drive anchors 700 into and through the bladder wall 2 and into the pelvic floor. To move the anchor driver arms 3461 to the position shown in FIG. 8, driver actuating rod or band 3261 and driver opening rod or band 3260 may be moved proximally, which can effect proximal movement of driver actuating screw pin 3465, and correspondingly, anchor driver arms 3461 and anchors 700, so as to drive anchors 700 into the tissues as shown. The proximal movement of driver actuating rod or band 3261 and driver opening rod or band 3260 may be effected by any suitable control and mechanism associated with handle assembly 3100, such as by pressing anchor driving lever 3102 to actuate a suitable associated mechanism within handle assembly 3100 (see FIG. 3). It may be desirable for there to be a direct mechanical linkage or connection between anchor driver lever 3102 and driver actuating rod or band 3261 and driver opening rod or band 3260, so as to provide the surgeon with tactile feedback through anchor driver lever 3102 as to the driving and seating of anchors 700 in the tissues.

It can also be seen in FIG. 8 that tails 3433 of balloon harness 3430 may be held by harness hooks 760 of anchors 700. Thus, when anchors 700 are driven into the tissues, tails 3433 of balloon harness 3430 may be attached at each anchor site, within the bladder and about the bladder opening. Anchors 700 may comprise barbs or any other suitable lodging structures on their shafts, so as to cause them to be lodged in and resist withdrawal from the tissues of the pelvic floor.

Figure 16:
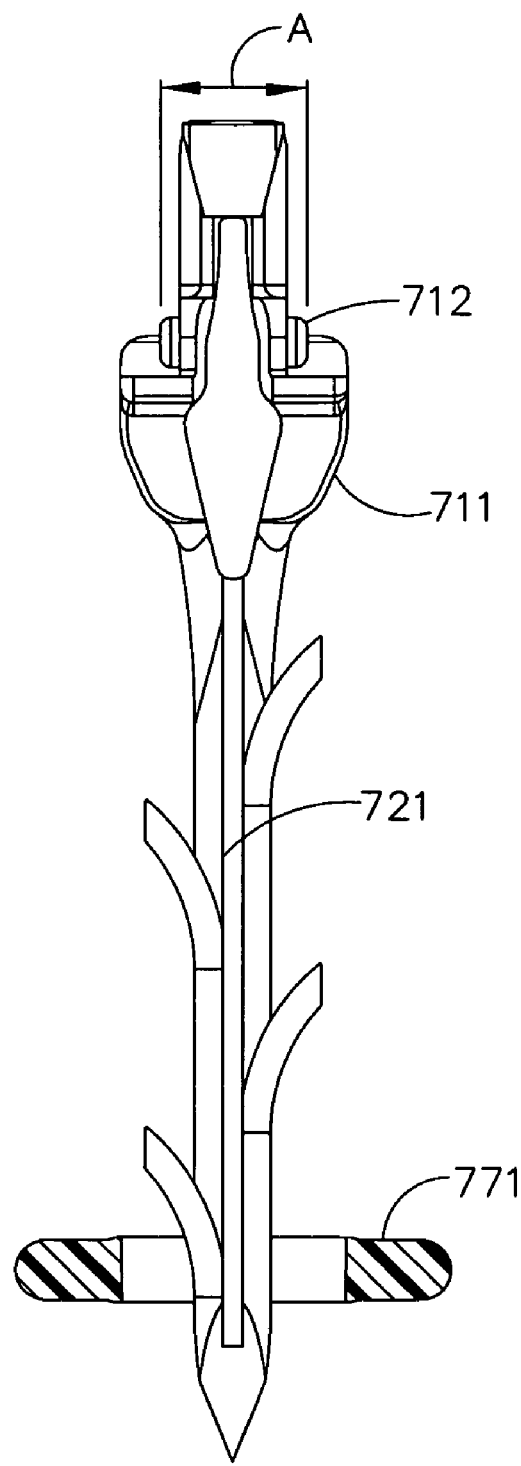
FIG. 16 is a perspective view of an exemplary version of an anchor shown with an anchor guide shown in cross section and positioned at the forward end.
Figure 16A:
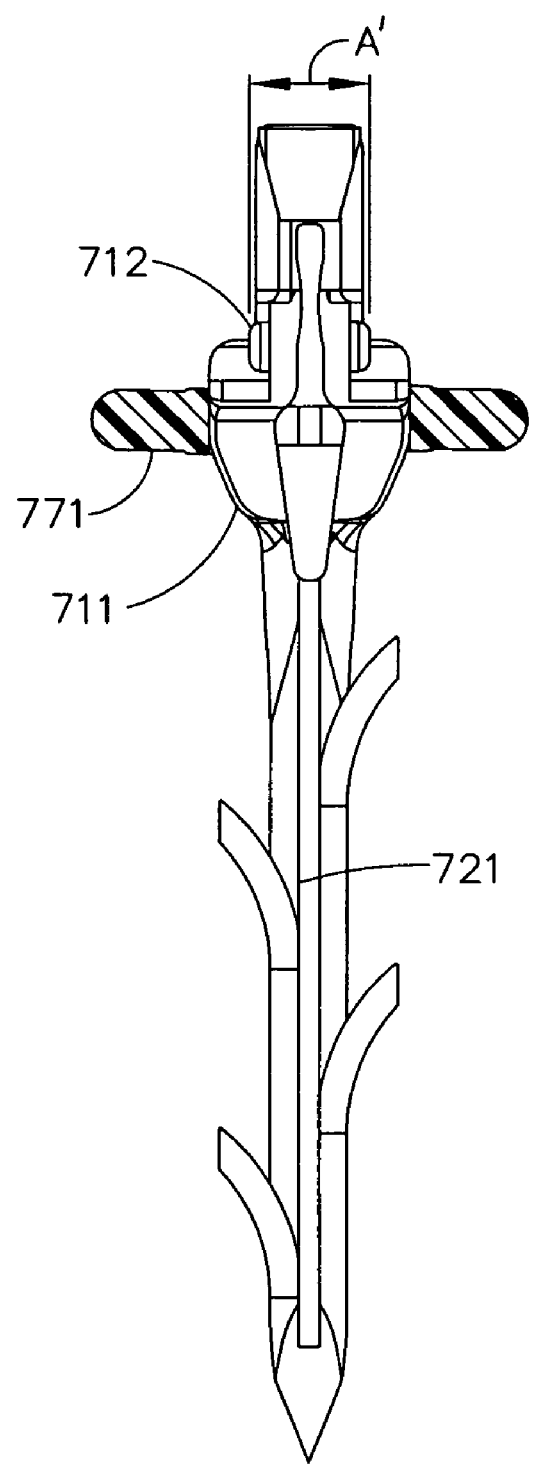
FIG. 16A is a front perspective view of an exemplary version of an anchor shown with an anchor guide shown in cross section and positioned at the rearward end.

The present exemplary version includes exemplary mechanisms for guiding anchors 700 during driving, and releasing anchors 700 from anchor driver arms 3461 upon or after driving. FIGS. 16 and 17D depict an exemplary anchor 700 and anchor guide 770. As previously described and as may be seen in FIG. 5A, anchor guide axle pins 771 may be retained in guide axle pin notches 3449 in anchor guide yokes 3448 of positioner arms 3441, by anchor guide retainer wires 3250. Referring again to FIGS. 16 and 17D, anchor guides 770 may include keyway features 772, with which longitudinal keyway mating features 721 of anchors 700 cooperate, such that anchors 700 may be guided through anchor guides 770 as they move downwardly during driving into the tissues. It will be appreciated that anchors 700 may be provided with a keyway feature and that anchor guides 770 may be provided with mating features associated therewith. In a further version, the anchor guides 770 and the anchors 700 may be provided with a combination of keyway mating features and keyway features to guide the anchor 700 through the anchor guide 770. Anchors 700 may also include flexing disengagement sections 711 as shown in FIG. 16. When anchors 700 are driven (downwardly, with respect to the figures) through anchor guides 770 to where such flexing disengagement sections 711 contact the sides 773 of anchor guides 770, flexing disengagement sections 711 can be urged inwardly, toward each other where, for example, the distance between the disengagement sections 711 may be reduced. This correspondingly can move anchor axle pins 712 inwardly, as illustrated in FIG. 16 and 16A shown moving from A to A', which can cause them to disengage from anchor yokes 3462 of anchor driver arms 3461, effecting the release of anchors 700 from anchor driver arms 3461.

Referring to FIGS. 8-10 and 15, as part of an anchor releasing step, anchor guide retainer wires 3250 may be withdrawn in a proximal direction back through retainer wire bores 3451 so that anchor axle pins 771 can be released from guide axle pin notches 3449 in positioner arms 3441. Referring again to FIGS. 16 and 17D, anchor 700 and anchor guide 770 may be formed with cooperating features such that anchor guide 770 may function as a washer, anchor head or other holding force distributing, and/or and penetration limiting, structure about the rearward end 710 of anchor 700, upon the release of these members from the end effector; see FIGS. 8-9A and 10.

As noted above, in the exemplary version anchor guide retainer wires 3250 may be withdrawn in order to release anchor guide axle pins 771 and correspondingly anchor guides 770 from positioner arms 3441. Anchor guide retainer wires 3250 may be withdrawn proximally within the tube assembly by any suitable means including a suitable mechanism within handle assembly 3100 to which anchor guide retainer wires 3250 are linked or connected. It will be appreciated that in the exemplary version described herein, anchor guide retainer wires 3250 must be withdrawn to release anchor guides 770 from positioner arms 3441 after the anchors have been driven into tissues, before positioner arms 3441 may be closed, but that a variety of other mechanisms for releasing anchor guides, or for releasing anchors from guide structures, are possible.

Still referring to and comparing FIGS. 8, 9, 10, 15, and 24, following the release of anchors 700 from anchor driver arms 3461 in the exemplary version as described above, anchor driver arms 3461 may be moved distally by distal motion of driver actuating rod or band 3261 and driver opening rod or band 3260, which act upon driver actuating screw pin 3465 and correspondingly anchor driver arms 3461. Anchor driver arms 3461 may then be closed or retracted by holding driver actuating rod or band 3261 substantially stationary while moving driver actuating rod or band 3260 in a proximal direction, which pulls driver arm struts 3262 downwardly and inwardly (relative to the figures) via driver opening screw pin 3263, and pulls anchor driver arms 3461 downwardly and inwardly in a manner similar to that of the closing of an umbrella. Finally, positioner arms 3441 may be closed or retracted by moving positioner rod or band 3240 in a distal direction, which pulls positioner struts 3445 upwardly (relative to the figures) via positioner actuating pins 3446, and correspondingly pulls positioner arms 3441 upwardly (relative to the figures) and inwardly in a manner similar to that of the closing of an umbrella, upside-down. Following the closing of the anchor driver arms and positioner arms to the position shown in FIG. 10, the portions of the end effector assembly including the positioner assembly 3440 and anchor driver assembly 3460, and tube assembly 3200, may be withdrawn in an antegrade direction downwardly (relative to the figure) out of the bladder, out of the urethra, and out of the patient, leaving behind only balloon harness 3430 with guide wire 3230, attached at tails 3433 within the bladder by anchors 700 as shown in FIG. 11. It will be appreciated that any suitable number of rods or bands may be used to actuate the instrument 3000 such as, for example, by using one rod or band to actuate a positioner assembly and a second rod or band to operate a driver assembly in association with a spine member.

It will be apparent to persons skilled in the art that a variety of mechanisms might be comprised by handle assembly 3100 and configured and adapted to transmit longitudinal (distal and proximal) forces and movement to an end effector assembly 3400, in order to effect and transmit the forces and movement therein necessary to actuate the exemplary embodiments as described above.

Referring again to FIG. 15, it can be seen that a sheath 3270 may encase tube assembly 3200. Sheath 3270 may be formed of any suitable biocompatible polymer or other biocompatible material, and may be provided with a suitable hydrophilic, lubricating and/or anti-bacterial coating. Sheath 3270 also may be internally lubricated or be formed of a suitably low-friction or self-lubricating material, and/or otherwise be fashioned so as to be flexible and slidable in distal and proximal directions on the instrument, so that it may be slid in a distal direction over end effector assembly 3400 so as to encase the components thereof to ease insertion into and retraction from the urethra, and slid in a proximal direction to expose the operable components of end effector assembly 3400 during actuation inside the bladder.

In a further version, the end effector assembly 3400 may be encased by an end sheath 3990 to ease insertion into the urethra (FIG. 3A). The end sheath 3990 may be a flexible tube, sealed at one end, which is rolled radially prior to use. Upon application, the sealed end of the end sheath 3990 may be applied to the distal end of the end effector assembly 3400, where the length of the flexible tube may then be unrolled down the length of the end effector assembly 3400 to substantially encase all or a portion of the end effector assembly 3400. The end sheath 3990 may also include one or a plurality of sutures 3992 extending along the length of the flexible tube. The sutures 3992 may project from the unsealed end of the end sheath 3990 such that a grasper, or other suitable device inserted via a cannula or the like, may grab the exposed length of suture 3992 and, by pulling distally, re-roll and remove the end sheath 3990. Following removal of the end sheath 3990, via a cannula or the like, the end effector assembly 3400 may be operated as disclosed herein.

Figure 12:
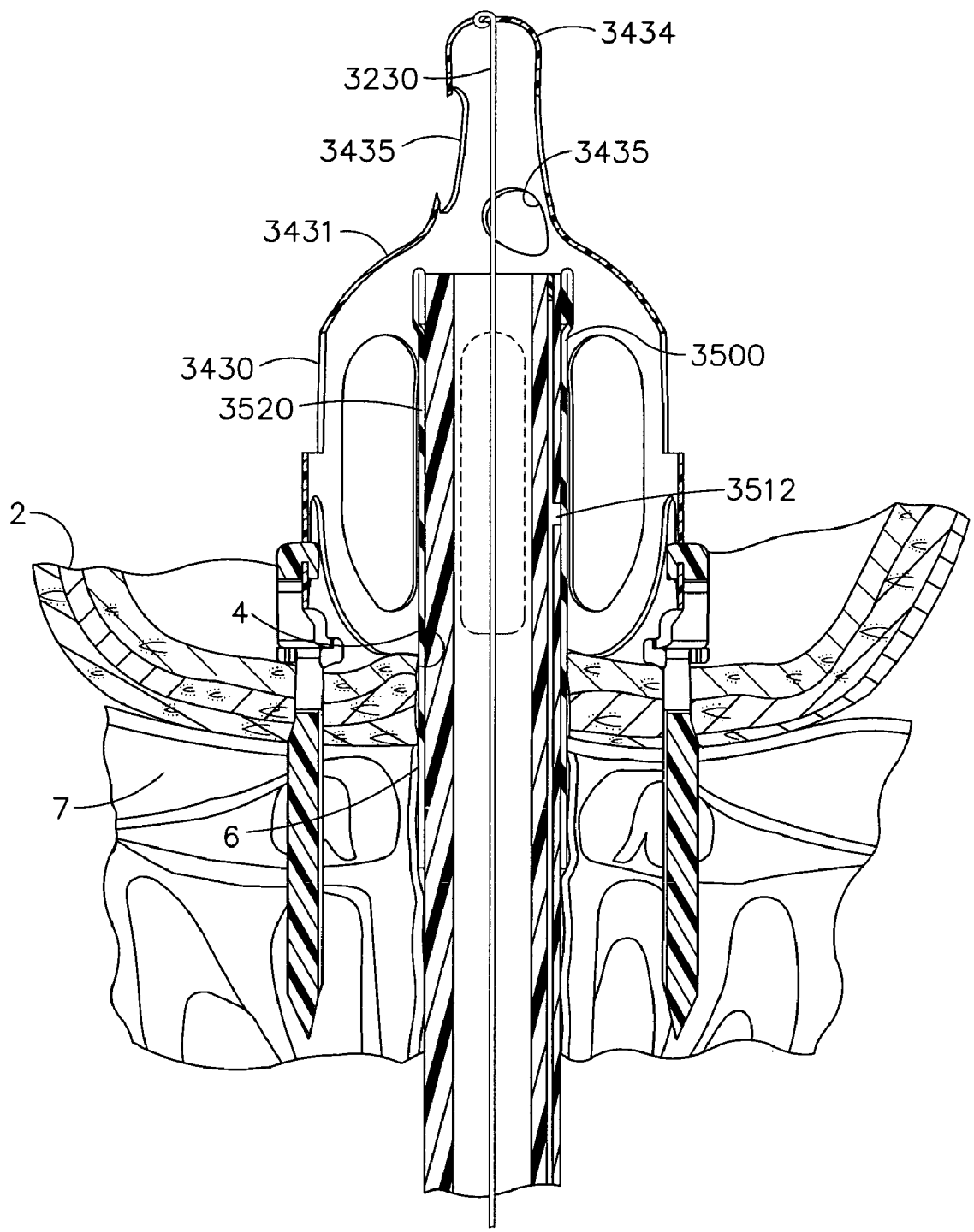
FIG. 12 is a longitudinal cross-sectional view of the balloon harness assembly of FIG. 11 with a balloon catheter shown inserted therein.
Figure 13:
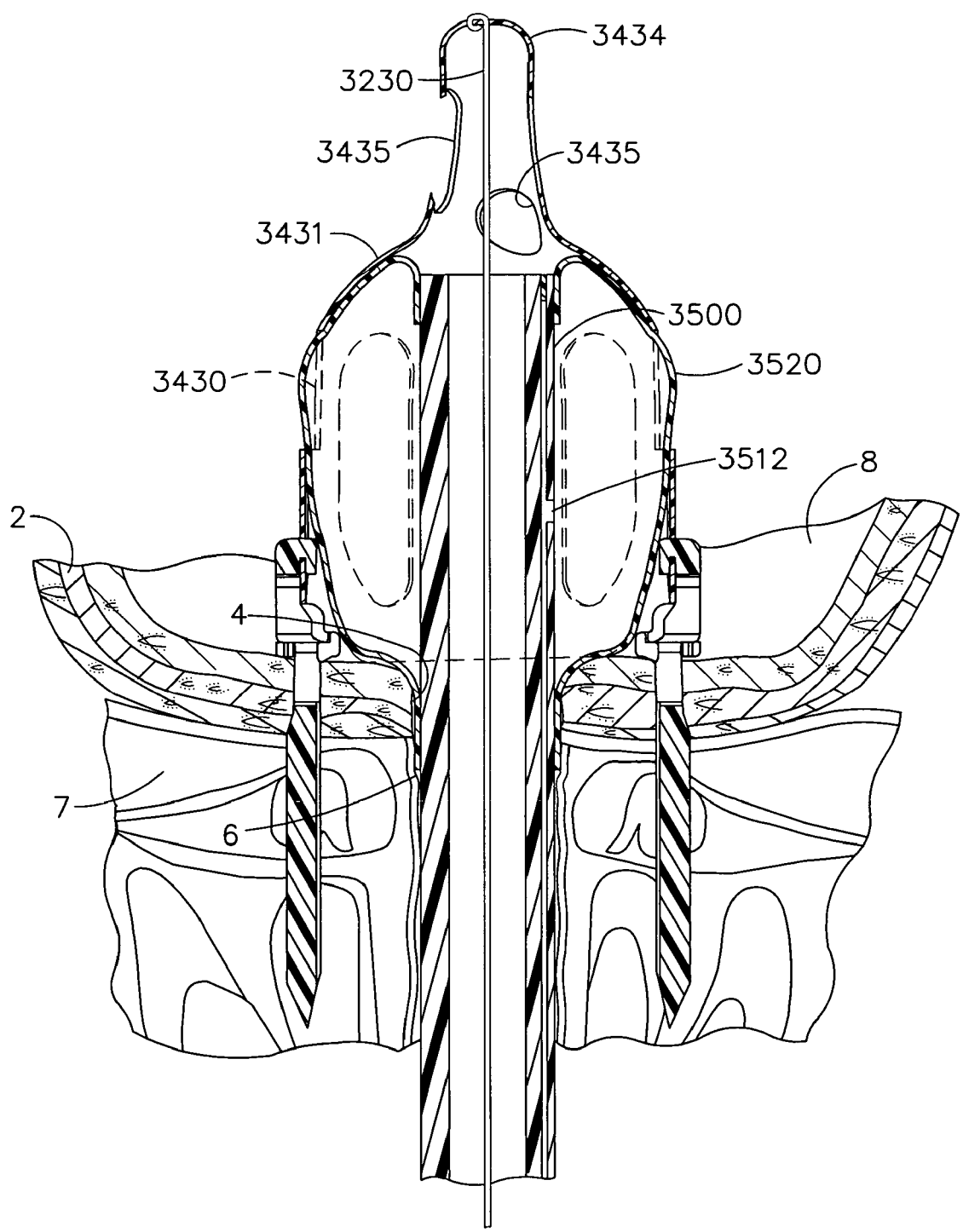
FIG. 13 is a longitudinal cross-sectional view of the balloon harness assembly and balloon catheter shown in FIG. 12, after the balloon of the balloon catheter assembly has been inflated.

As shown in FIG. 12, following attachment of the balloon harness with the bladder and withdrawal of components from the patient as described above, a balloon catheter assembly 3500 having a central passage therethrough, may be introduced onto the proximal end of guide wire 3230 and inserted and guided upwardly (in a retrograde direction) into and through the urethra and into the bladder, until balloon 3520 contacts the inside of balloon harness collar 3431 of balloon harness 3430. Referring to FIG. 13, balloon 3520 may be inflated with any suitable fluid. As balloon 3520 is inflated, its upper surfaces may form a substantially fluid-tight seal against the inside of balloon harness collar 3431, and its upward and horizontal expansion may be constrained by balloon harness 3430. As a result, balloon 3520 can be caused to expand downwardly with inflation, thereby contacting and exerting downward pressure against the bladder wall in an area surrounding the bladder opening 4, approximately equal to the pressure within the balloon. As a further result, an area of bladder wall 2 surrounding the bladder opening 4 can be urged against the pelvic floor 7 in an area surrounding the urethra opening 6, with the respective openings of the bladder and urethra 4, 6 substantially aligned. Additionally, the bladder opening 4, pelvic floor 7 and urethra opening 6 can be sealed off so as to prevent urine and other materials collecting in the bladder during recovery and healing from escaping the bladder and entering the abdominal cavity.

The balloon harness 3430 and balloon catheter assembly 3500 may then be maintained in place (the balloon catheter assembly may be periodically replaced with a fresh balloon catheter assembly and inflated as described above, as may be required or desired), for a period of time necessary for the tissues of the bladder wall 2 and the pelvic floor surrounding respective openings of the bladder and urethra 4, 6 to effectively knit together. A suitable period of time for knitting may be approximately two weeks, but may vary depending upon the needs and health of the individual patient and individual preferences of the surgeon and the patient. During this period, urine and other materials may be drained from the bladder through drainage holes 3435 in the harness tip 3434 of balloon harness 3430, and then out through the central passage of the catheter. During recovery and healing, the catheter tube may be connected at a proximal end to a urine collection bag (not shown).

Figure 14:
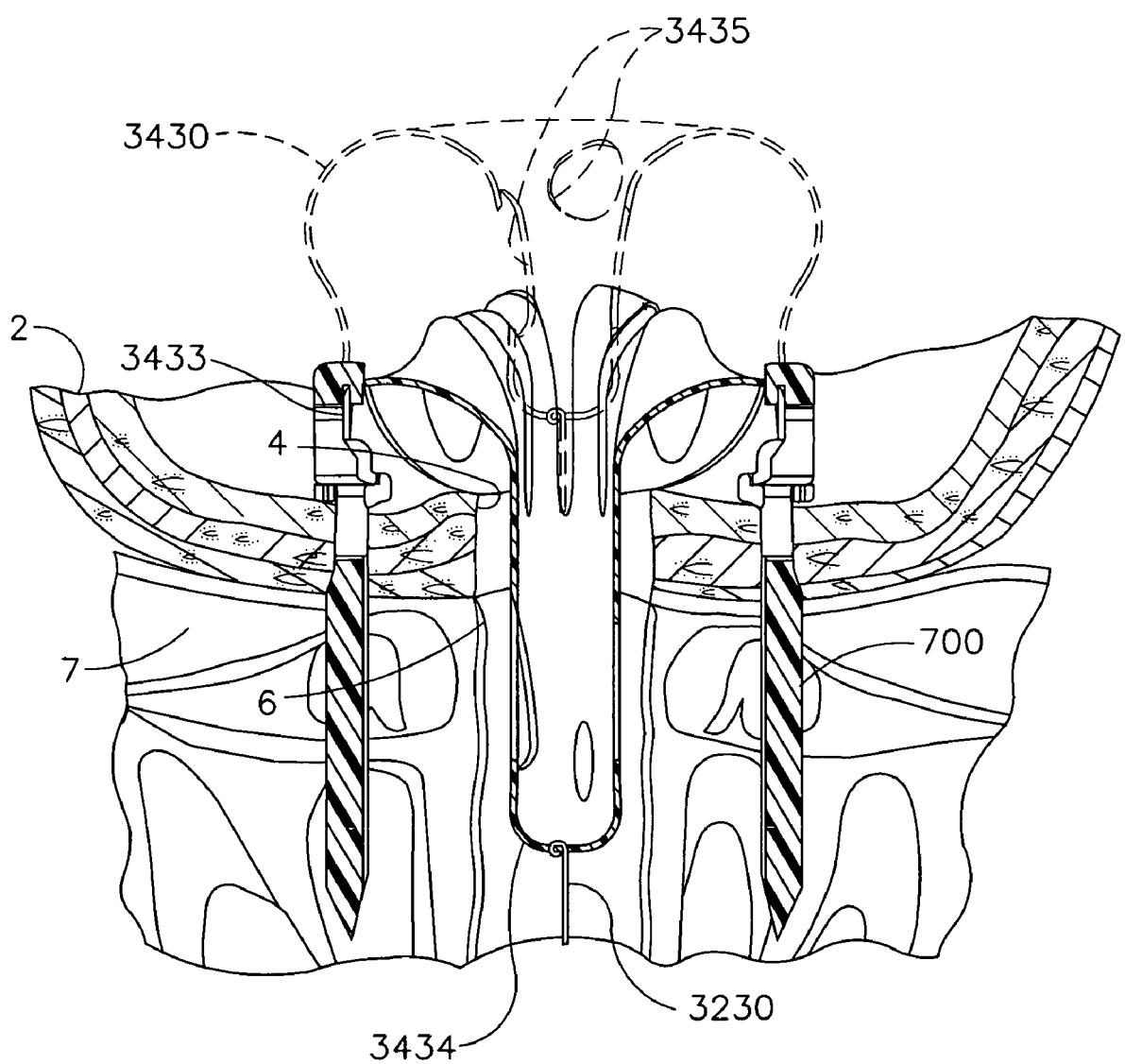
FIG. 14 is a longitudinal cross-sectional view of the balloon harness assembly of FIG. 12 as it is being everted for removal following removal of the balloon catheter assembly of FIG. 12.

Following the period of time necessary for the tissues of the bladder wall and pelvic floor to effectively knit together, the balloon 3520 may be deflated and the balloon catheter assembly 3500 withdrawn and removed. Next, referring to FIG. 14, guide wire 3230 may be withdrawn. Because the distal end of guide wire 3230 may be affixed within harness tip 3434 of balloon harness 3430, withdrawing guide wire 3230 can cause balloon harness 3430 to evert. A suitable manner of attachment releasable between balloon harness tails 3433 and anchors 700 such as described in pending application Ser. No. 11/094,606 will allow for the release of tails 3433 from anchors 700 upon such everting, and balloon harness 3430 may be withdrawn downwardly (in an antegrade direction) by withdrawing guide wire 3230, and out of the patient. Thus, only anchors 700 can be left behind. As described in pending application Ser. No. 11/094,606, anchors 700 may be formed of a bioabsorbable material, and if so formed, can dissolve within the body.

It may be appreciated that the combination of a balloon harness structure anchored to the pelvic floor as depicted and described herein, constraining and holding the inflated balloon of a balloon catheter, can have the desirable effect of constraining the catheter from substantial axial or longitudinal movement within the urethra during the period required for anastomosis. Versions of the balloon harness 3430 described herein are directed to an efficient and effective means of providing support for a balloon catheter assembly 3500 in performing anastomosis procedures.

Figure 17A:
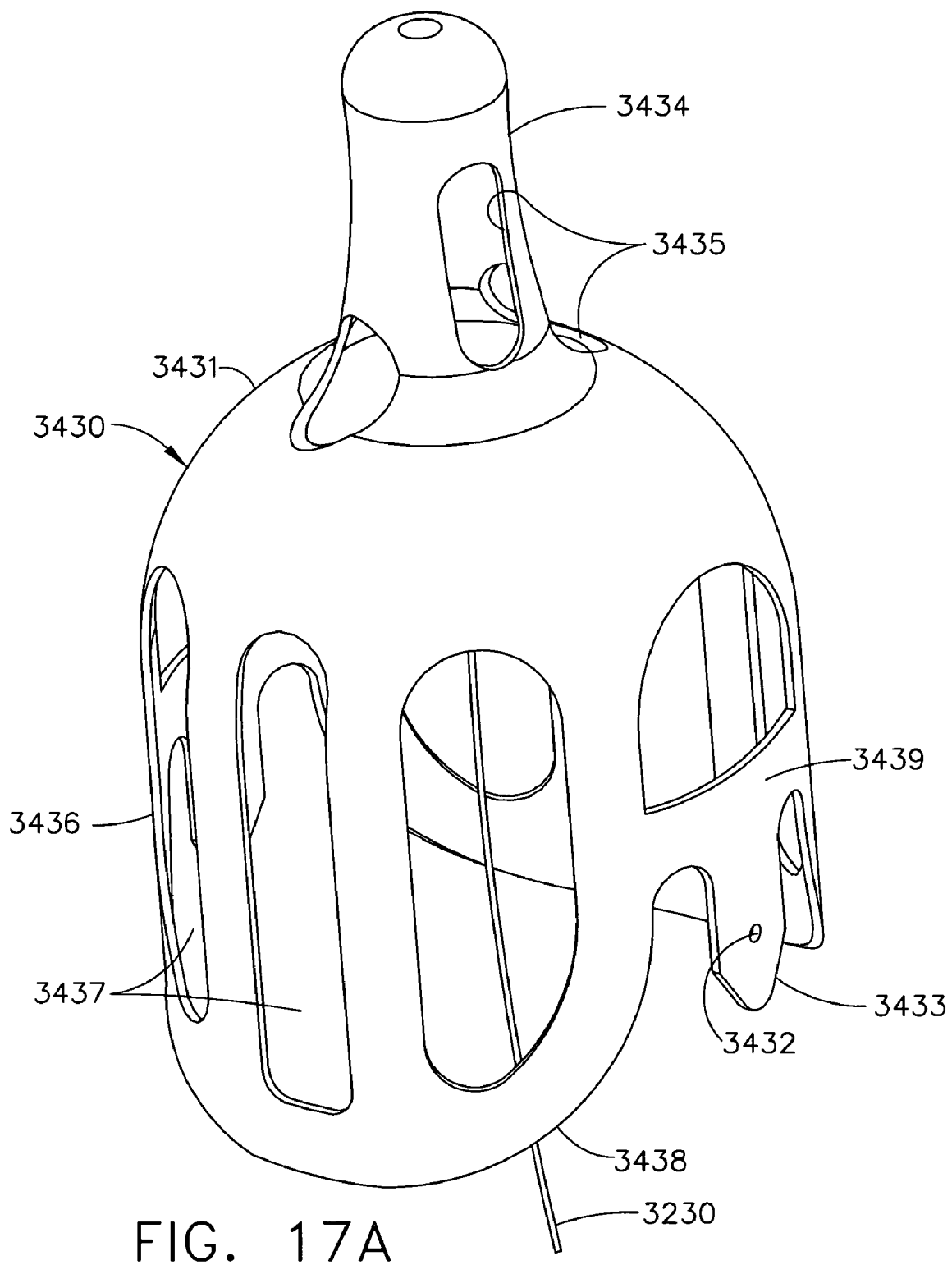
FIG. 17A is a perspective view of an exemplary balloon harness within the scope of the present invention.

Referring to FIGS. 12, 13 and 17A, balloon harness 3430 may be anchored within the bladder by harness tails 3433 attached to anchors 700 (FIG. 16). Balloon harness 3430 then may be used to hold, and allow for urine drainage through, balloon catheter assembly 3500 via drainage holes 3435 in harness tip 3434. Balloon harness 3430 may also provide restraining support to a balloon 3520 of a balloon catheter assembly 3500 retained therein by cradling the balloon 3520 within the balloon harness collar 3431 and skirt 3436, providing for concentration and increase in the amount of downward pressure that may be applied to the bladder wall via the balloon. Versions and features of a balloon harness 3430 will be described herein.

Balloon harness 3430 may be formed from any suitable biocompatible material such as, for example, a polymeric material. For example, the body of balloon harness 3430 may be formed, for example, by dipping a suitably shaped and sized mandrel into a material vat of uncured liquid polyurethane product such as, but not limited to, Pellethane 2363 90AE, manufactured by Dow Plastics, Midland, Mich. Rotational and/or heated air drying techniques may be used to control wall thickness. Alternatively, the body may be molded with a suitable polymeric material, with wall thickness being controlled in the molding process.

In order to cut and/or form the various features and thereby complete the manufacture of the exemplary balloon harness 3430 shown in FIG. 17A, a low powered laser may be employed to cut features of a dipped body, or molding techniques may be incorporated into the body molding process employed, or any other suitable forming means may be employed. To cut features using a laser, a pattern computer file may be used, in combination with a low powered laser, that feeds the linear axis of the laser and rotary actuator to melt a path on the shell (held on a mandrel) that creates, for example, drainage holes, expansion holes, harness length, harness tail, anchor hook holes and/or skirt shape.

If the balloon harness is formed having a wall thickness that is too small, this may result in a harness with insufficient strength and balloon restraining capability. Conversely, wall thickness that is too great may result in a harness that is not sufficiently flexible so as to be foldable within the end effector and/or easily everted for purposes of withdrawal from the patient.

Still referring to FIGS. 12, 13 and 17A, balloon harness 3430 may be provided with a hollow harness tip 3434 to allow drainage of urine from the bladder. In one version, harness tip 3434 may be sized to effectively fit over the distal portion of a balloon catheter assembly 3500 that may be inserted into the balloon harness 3430. For example, a balloon catheter assembly 3500 may be inserted into and retained within balloon harness collar 3431 and skirt 3436 such that the distal portion of the balloon catheter assembly 3500 extends into the harness tip 3434. Harness tip 3434 may be sized to effectively fit over, for example, a 14 Fr or 18 Fr catheter.

Harness tip 3434 may be adapted to permit the drainage of urine from the bladder through a balloon catheter assembly 3500 inserted into balloon harness 3430. For this purpose, harness tip 3434 may be provided with one or more drainage holes 3435 to allow the ingress of fluid. The drainage holes 3435 may include, for example, one or more holes positioned wholly or partially on the balloon harness collar 3431 and/or harness tip 3434. Drainage holes 3435 may be of varying sizes and/or shapes and may be configured to effect efficient drainage for any suitable balloon catheter assembly 3500 that may be used in combination with balloon harness 3430. Versions of drainage holes 3435 may be, for example, of circular and/or elliptical shapes in a staggered configuration to provide for the efficient drainage of fluid. In the example shown in FIG. 17A, the drainage holes 3435 may include four holes positioned approximately 90° apart around the circumference of the harness tip 3434 and may alternate between an elliptical shape and a circular shape and may be staggered axially. It will be appreciated that the shape, configuration, placement, and/or design of the drainage holes 3435 may vary depending on the material used, the thickness of the material and the size of the harness tip.

Still referring to FIG. 17A, the balloon harness collar 3431 may be, in one version, an increasing radius portion of the balloon harness 3430 adjacent to the base of harness tip 3434, that may extend outwardly therefrom until the unstretched radius of the balloon harness 3430 becomes substantially constant. The balloon harness collar 3431, in the version depicted, is the portion of the balloon harness 3430 that transitions between the harness tip 3434 and the skirt 3436. The balloon harness collar 3431 may retain the balloon 3520 of the balloon catheter assembly 3500 and provide support force that is substantially equal and opposite to the force applied by the balloon 3520 to the bladder wall at the anastomosis site. It may be preferable to minimize the extension of any drainage or expansion holes substantially into the collar region because this may lead to a reduction in the downward holding force the harness may exert.

The balloon harness may have skirt 3436, comprising the portion of the balloon harness 3430 adjacent to the balloon harness collar 3431 extending to the bottom-most point (with respect to FIG. 17A) of the balloon harness 3430. The balloon harness 3430 may provide hoop loading to constrain the balloon 3520 therein. For example, when the balloon 3520 is inflated, the skirt 3436 may be of sufficient length so that its bottom edge (with respect to the figures) lies below the vertical mid-point of the balloon 3520, so as to prevent balloon 3520 from sliding out from under balloon harness 3430. Alternatively, skirt 3436 may be provided with varying radii to achieve a similar purpose.

Skirt 3436 also may be provided with expansion holes 3437 formed therein. Expansion holes 3437 may be sized and situated so as to permit portions of balloon 3520, upon inflation, to bulge outwardly through expansion holes 3437, to provide additional support and restraint to the balloon 3520 retained therein, and to prevent the balloon harness 3430 from shifting or slipping off balloon 3520, or prevent balloon 3520 from shifting or slipping out from under the harness. Expansion holes 3437 may include one or a plurality of holes, in one or a plurality of tiers, and may be arranged horizontally, vertically, as a circular cut-out, as an elliptical cut-out, or combinations thereof. The size and placement of expansion holes 3437 may be selected based upon the extent of balloon bulge-through desired. For example, providing a skirt 3436 with four large vertical expansion holes 3437 may provide more substantial bulge-through than a skirt 3436 having eight smaller vertical expansion holes 3437. Altering the extent of bulge-through of the balloon 3520 by altering the size and placement of expansion holes 3437 may allow tailoring of the amount of balloon support desired and the amount of downward pressure that may be applied by the balloon to the bladder wall. For example, if extensive bulge-through is permitted, this may have the effect of limiting the amount of downward pressure that the balloon may exert on the bladder wall. If expansion holes 3437 are situated uniformly and/or symmetrically about skirt 3436, this may cause harness 3430 to promote and/or effect uniform expansion and uniform expanded shape of a balloon at the area of contact with the bladder wall.

Still referring to FIG. 17A, skirt 3436 of the balloon harness 3430 may be provided with at least one extension 3438. The extension 3438 may be elliptical in shape and of a length sufficient to reach below the vertical midpoint of a balloon. Provided an extension 3438 reaching below the vertical midpoint of the balloon may help prevent the balloon from slipping out of the balloon harness 3430 where, as the balloon 3520 expands, the extension 3438 cradles the balloon 3520 below the midpoint. It will be appreciated that the extension 3438 may be of any suitable shape and/or configuration suitable for cradling and retaining a balloon 3520 therein.

FIG. 17A depicts two extensions 3438 configured to straddle and/or cradle a balloon 3520 therebetween. At the juncture 3439 of the extensions 3438 there may be positioned a harness tail 3433 adapted for attachment to an anchor 700. The harness tail 3433 may be a strip of material integral with and extending downwardly (with respect to the figure) from the skirt 3436. In the version shown, locating the harness tail 3433 at the juncture 3439 of the extensions 3438 may provide additional support for the balloon between the skirt extensions 3438. For example, as the balloon 3520 expands within the skirt 3436, the skirt extensions 3438 may deform and cradle the balloon 3520 as they are pushed outward. The length of the harness tail 3433 will affect the performance of the strap. A short tail length can minimize the extent to which the balloon may expand below the harness and thereby limit the area of the tissues on which the balloon may exert pressure. Conversely, a longer tail length can allow for more of the balloon to expand outwardly below the harness, increasing the area on which pressure is exerted on the tissues, but decreasing the maximum amount of pressure that may be exerted. The dimensions of the tail will also affect its tensile strength in holding the strap to the anchors while the inflated balloon is being restrained. The tensile strength of the tail (or combined tensile strength of the tails) should be considered so that it is a suitable multiple of the maximum downward holding force required, so as to provide an acceptable margin of safety.

Figure 10:
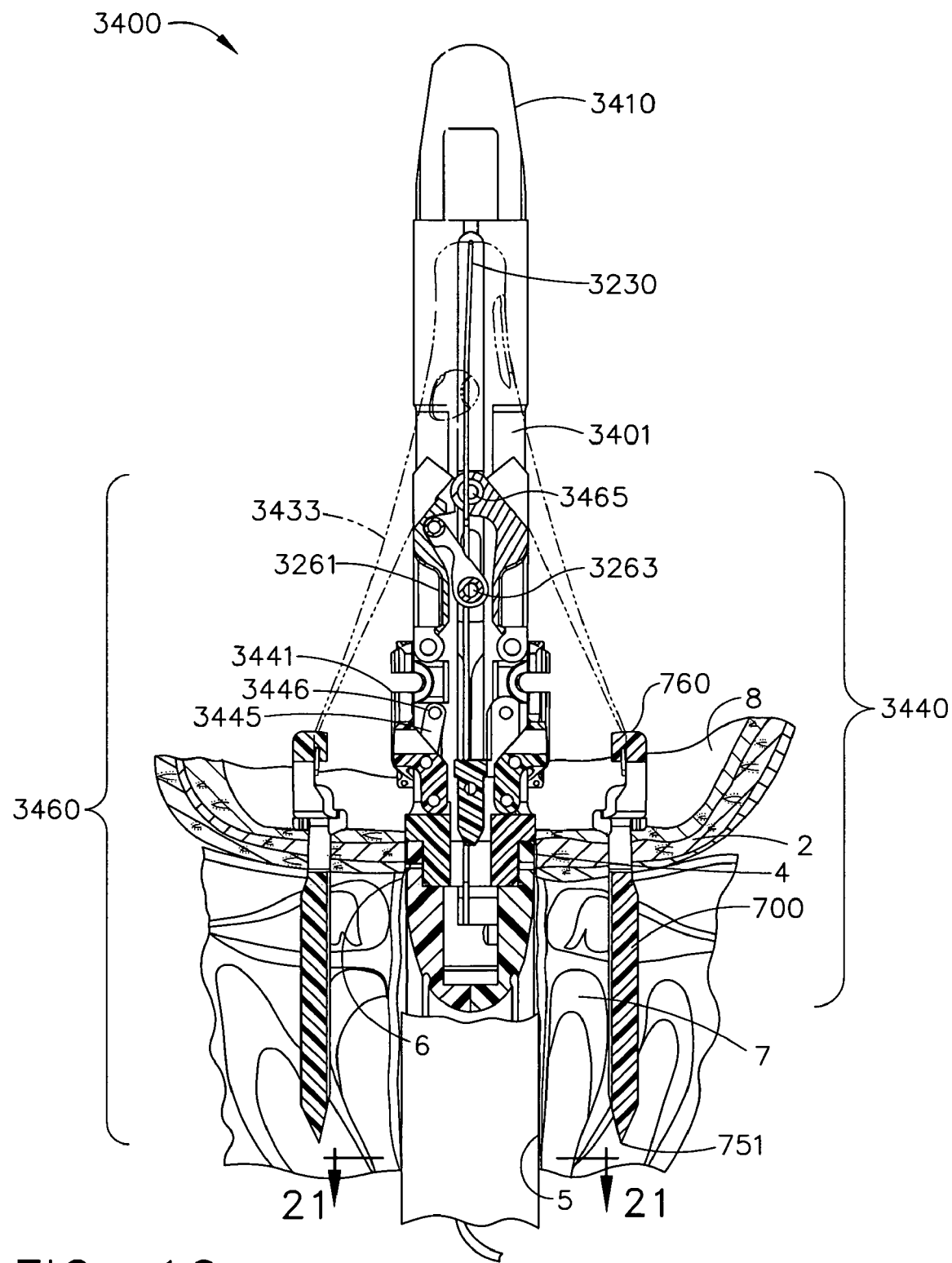
FIG. 10 is a longitudinal cross-sectional view of the end effector assembly shown in FIG. 3 after the driver arms have been closed and the positioner arms have released anchor guides and have been closed.
Figure 10A:
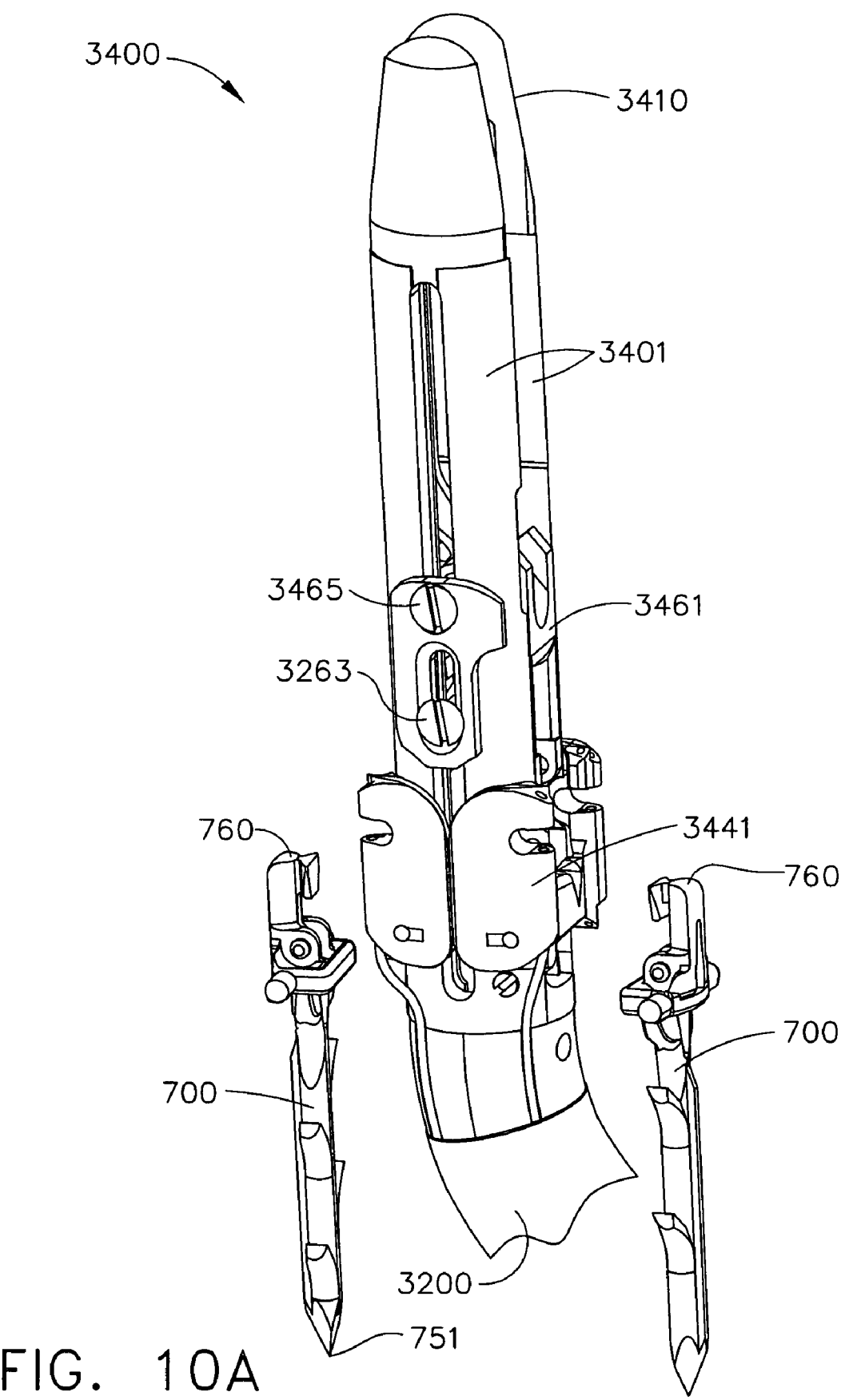
FIG. 10A is a perspective view of the end effector assembly shown in FIG. 10.
Figure 11:
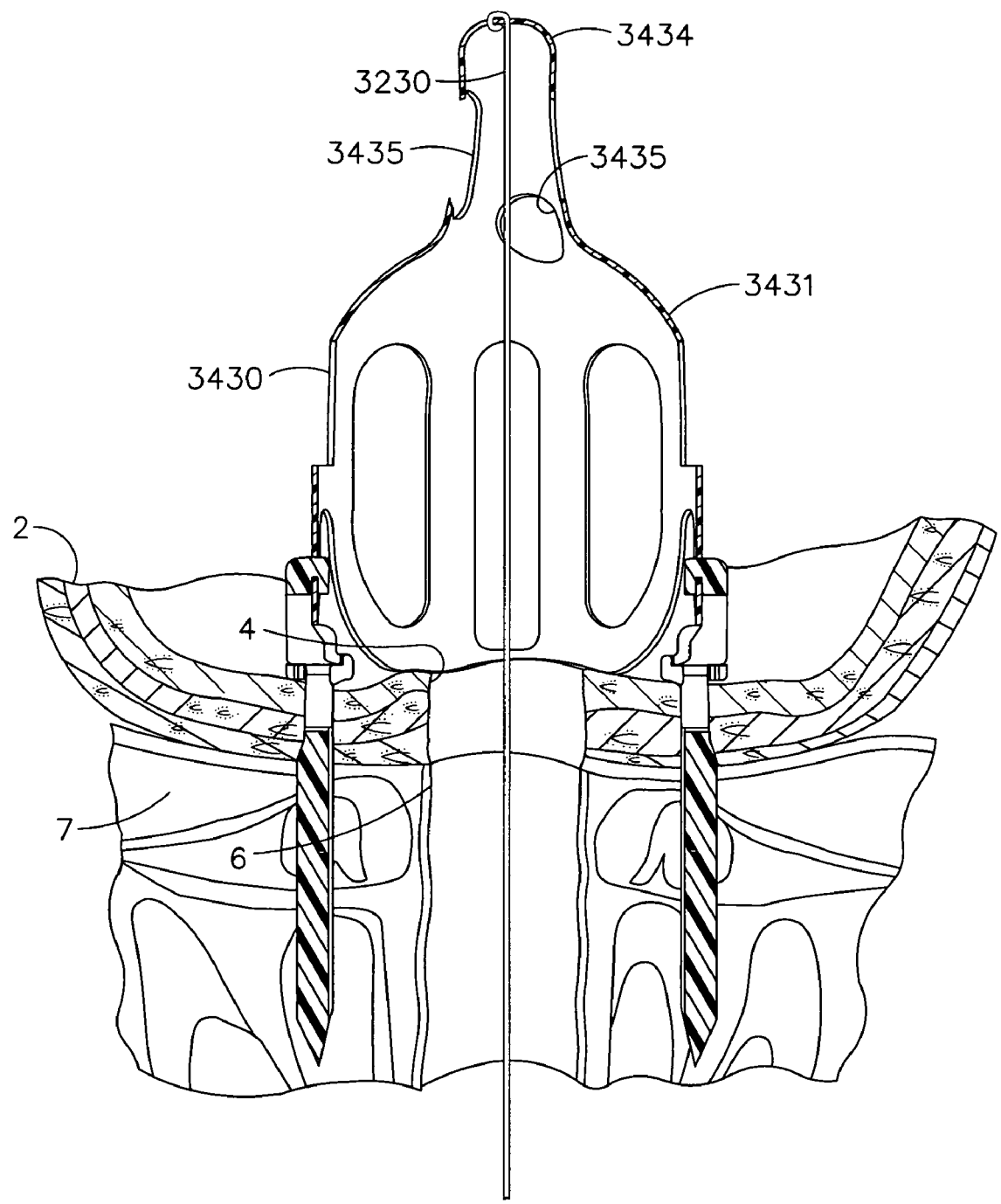
FIG. 11 is a longitudinal cross-sectional view of an installed balloon harness assembly.

Harness tail 3433 may be provided with at least one anchor hook hole 3432 therethrough to accept the insertion of a harness hook 760 of anchor 700 (FIGS. 10-11). Varying the length of the harness tail 3433 may allow for manipulation of the extent of balloon 3520 expansion below the skirt 3436 from inflation, and the resulting downward pressure applied by the inflated balloon against the bladder wall 2. As one possible mechanism for attaching harness tail 3433 to anchor 700, an anchor hook hole 3432 may be cut or formed in harness tail 3433. Anchor hook hole 3432 may be sized to stretch to accept insertion of a suitably sized harness hook 760. The harness hook 760 may be inserted therethrough before use, and may be retained therein with a suitable snap feature or friction fit between the anchor hook holes 3432 and hook 760 during the anastomosis procedure. Upon completion of use and final withdrawal of the balloon catheter, the harness tail 3433 and balloon harness 3430 having this exemplary attachment mechanism can be disengaged from the harness hook of the anchor by applying sufficient pulling/withdrawal force on the guide wire, everting the balloon harness and tail, and overcoming the resistance of the snap and/or friction fit between the anchor hook holes 3432 and the harness hook 760. The balloon harness 3430 can then be withdrawn from the bladder, leaving the anchors 700 behind. It will be appreciated that any suitable attachment system or method may be employed to provide a detachable connection between the anchor 700 and the balloon harness 3430. For example, harness tail 3433 may be formed without anchor hook hole 3432, and of a material that may be punctured at the desired location by a suitably shaped harness hook 760. If an anchor hook hole or puncturing attachment method is used with the harness tail, the size and shape of the hole or puncture will affect the tensile holding strength of the tail.

Still referring to FIG. 17A, the length of the harness may be, for example, about 0.925 inches as measured from the bottom of the skirt extension to the distal end of the harness tip. The length of the skirt may be, for example, from about 0.45 inches to about 0.65 inch, and it may be preferable for the bottom of the skirt extension to be below the balloon's vertical midpoint when the balloon is inflated to suitable pressure. The interior unstretched diameter of the skirt may be about 0.75 inches, or have any other constant or varying diameter. Harness tail 3433 may be, for example, about 0.13 inches in length. Anchor hook hole 3432 may be about 0.013 inch in diameter. A wall thickness of about 0.009 inch (assuming it is formed from the material specifically identified herein) may allow the balloon harness to have characteristics striking a suitable balance between strength and flexibility for use as described herein. Expansion holes 3437 may be include, for example, eight expansion holes situated about the circumference of the skirt 3436 such that upon inflation of the balloon 3520 the bulge-through of the apertures is substantially uniform although not necessarily symmetrical. A substantially consistent bulge-through may diminish the distortion of the balloon 3520 when inflated, thereby providing a more uniform zone of pressure on the bladder wall and around the bladder opening. Drainage holes 3435 may be sized to provide fluid ingress area substantially equivalent to that of an 18 Fr catheter.

As an alternative to the necessity for detachment from anchors and withdrawal of the balloon harness following the anastomosis procedure, a balloon harness may be formed from a suitable bioabsorbable material, with a time degradation characteristic that suitably corresponds to the time required for effective knitting of tissues in the anastomosis procedure. This would eliminate the necessity for a mechanical or structural release mechanism with respect to release of the balloon harness from the anchors, and reduce the number of components that must be withdrawn down through the urethra and out of the patient to complete the procedure following effective knitting of the tissues.

It will be appreciated that the balloon harness 3430 may be sterilized prior to use via autoclave, EtO, and/or with gamma radiation, where the effects of such sterilization techniques on the material may be considered in manufacturing the balloon harness 3430.

Figure 17B:
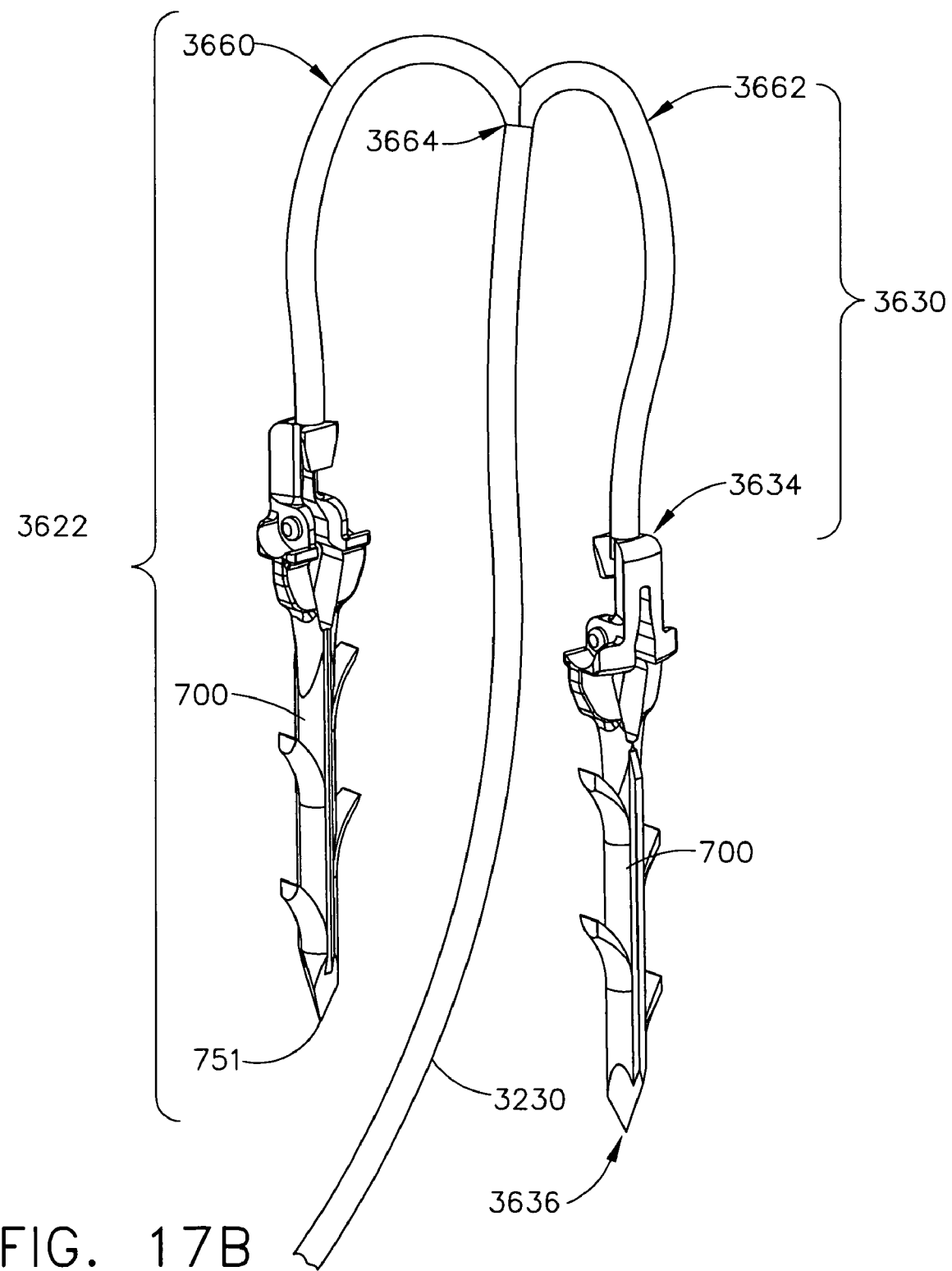
FIG. 17B is a perspective view of another exemplary balloon harness within the scope of the present invention.

Referring to FIG. 17B, another version of a balloon harness assembly in the form of strap harness assembly 3622 is depicted having a strap harness 3630 and at least one anchor 700 attached thereto. The anchor 700 may be provided with a rearward end 710 and a forward end 751. The strap harness 3630 may include a first strap 3660 and a second strap 3662 configured to retain a balloon of a suitably cooperating shape during an anastomosis procedure. The first strap 3660 and second strap 3662, with reference to the illustrated FIG. 17B, may be affixed proximally at one end to the rearward end 710 of the anchors 700.

The straps 3660, 3662 may be attached at the other end to a guide wire 3230 at a connection 3664. The straps 3660, 3662 may be integral with the guide wire 3230, or may be mechanically or adhesively attached thereto. When the strap harness assembly 3622 is deployed in substantially the same manner as other versions of a balloon harness assembly described herein, a balloon catheter assembly 3500 may be guided into the bladder by the guide wire 3230. The balloon catheter assembly 3500 may be inserted into the bladder along the guide wire 3230 until the balloon catheter assembly 3500 is fitted within the straps 3660, 3662.

Straps 3660, 3662 may be formed from any suitable biocompatible material, including but not limited to a polymeric material and/or suture material. The straps 3660, 3662 may be mechanically detachable from the anchors 700 or, for example, they may be partly or entirely constructed from a bioabsorbable material, such as Vicryl, a product of Ethicon, Inc., Somerville, N.J., that will dissolve within an appropriate period of time, leaving only guide wire 3230 to be removed at the completion of the anastomosis procedure. It will be appreciated that versions herein include providing for the mechanical release of the straps 3660, 3662 from the anchors 700, the use of a degradable material for any suitable element of the strap harness assembly 3622, and the use of one or a plurality of straps 3660, 3662 in combination with one or a plurality of anchors 700, with a suitably shaped balloon formed to fit therewithin.

Figure 17C:
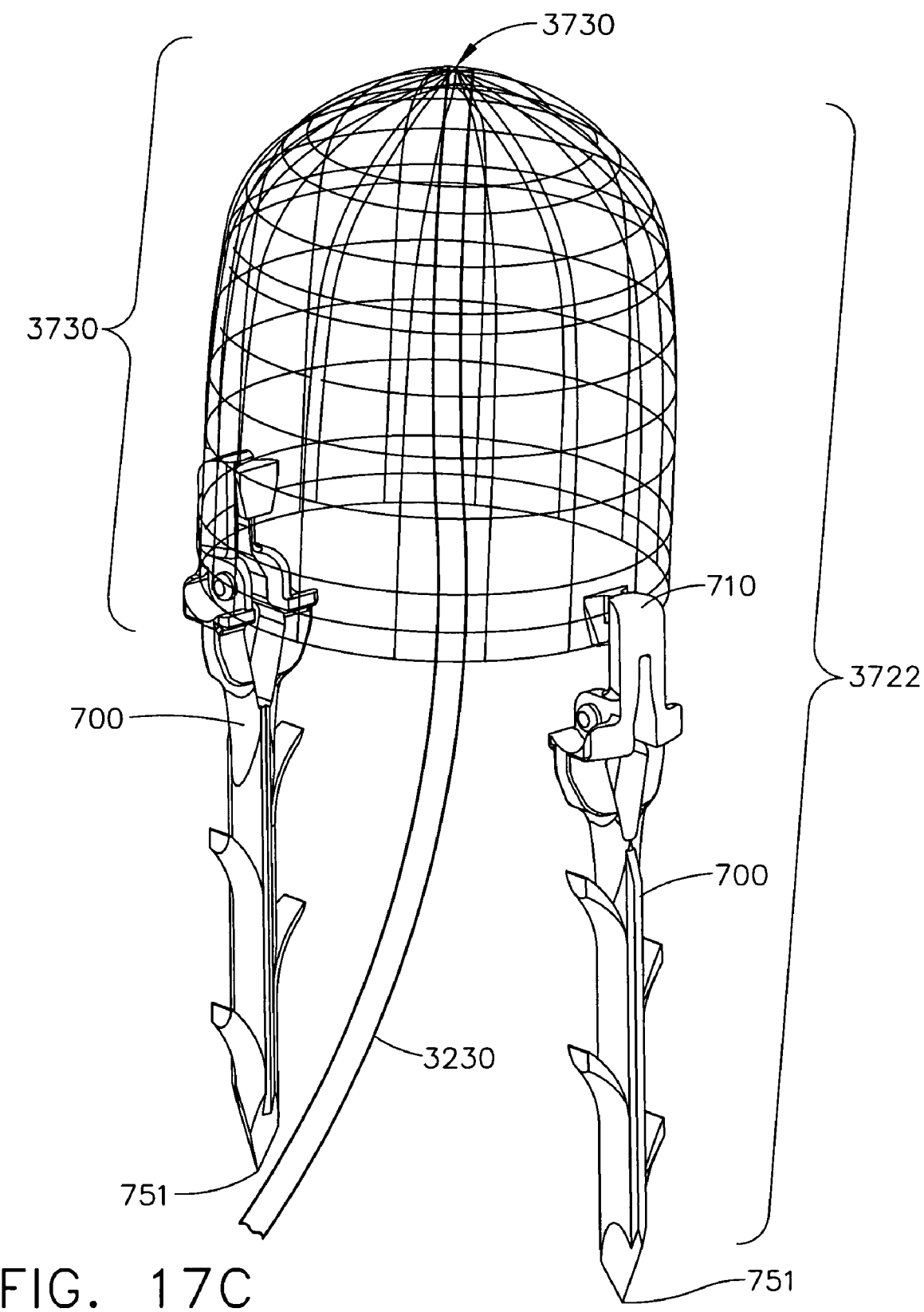
FIG. 17C is a perspective view of another exemplary balloon harness within the scope of the present invention.
Figure 17D:
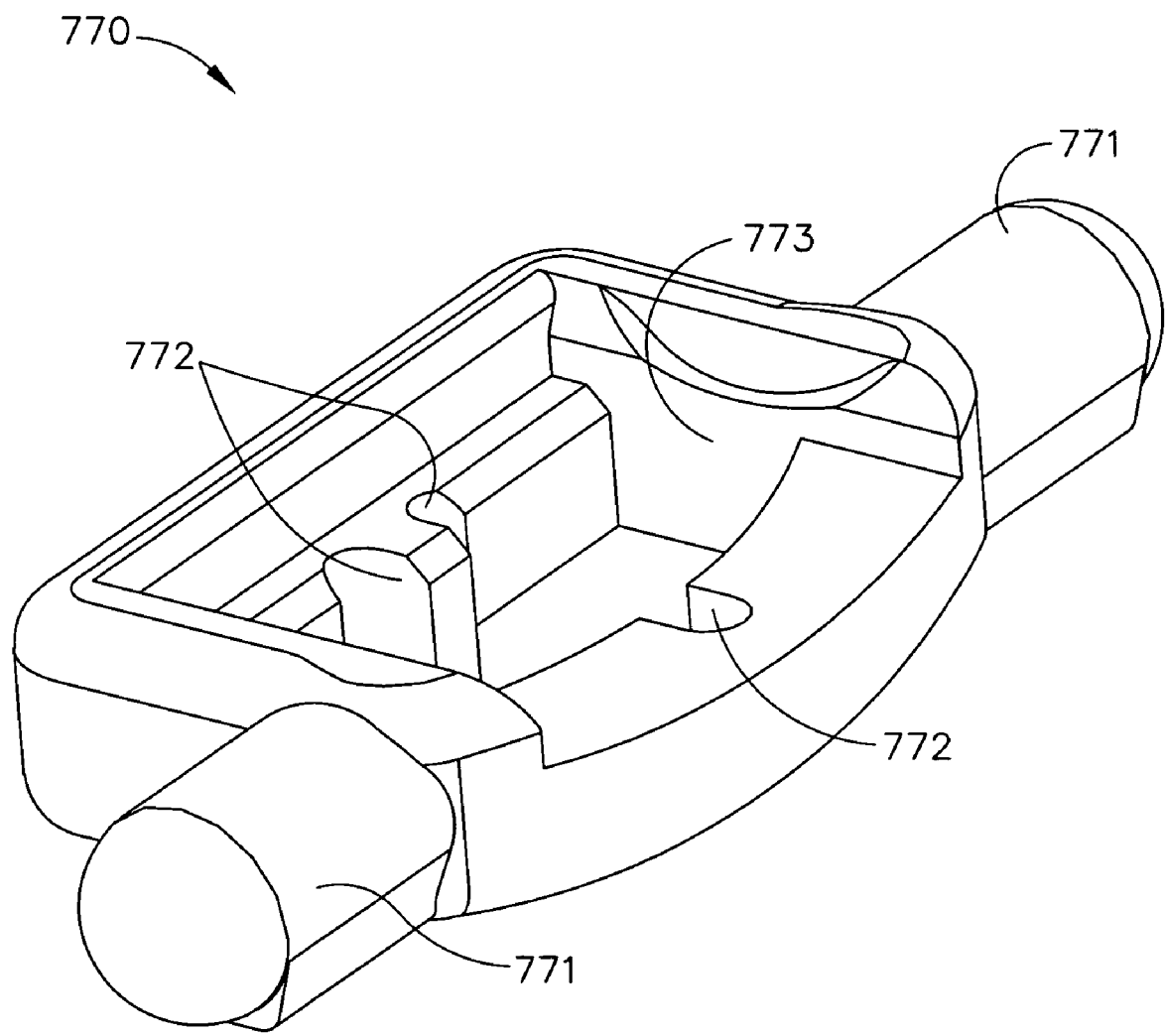
FIG. 17D is a perspective view of an exemplary version of an anchor guide that may be used with an instrument and/or method within the scope of the present invention.

Referring to FIG. 17C, another version of a balloon harness assembly in the form of a net harness assembly 3722 may include a net harness 3730 and at least one anchor 700 attached thereto. The anchor 700 may be provided with a rearward end 710 and a forward end 751. The net harness 3730 may comprise, for example, a mesh-like member formed of sutures or other mesh material suitably configured to retain a balloon. The net harness 3730 may be affixed proximally to the rearward end 710 of the anchors 700 with, for example, an adhesive connection, a mechanical connection, and/or with a bioabsorbable material, such as Vicryl. The guide wire 3230 may be connected to the net harness 3730 at the distal apex thereof, as illustrated, with, for example, an adhesive attachment, an integral construction, a mechanical connection, or with a bioabsorbable material, such as Vicryl.

Referring again to FIG. 17A, guide wire 3230 may be, for example, stainless steel, 0.0115 inches in diameter, and have a PolyTetraFluoroEthylene (PTFE) lubricating coating. Harness tip 3434 may be formed with a hole at its distal end or with any other suitable mechanism for locating and/or affixing the distal end guide wire 3230 therewithin. The hole may be utilized as a means to locate, install and/or affix guide wire 3230 within harness tip 3434. Guide wire 3230 may be, for example, inserted through a hole at the distal end of harness tip 3434 and have its distal end held therein by a catching feature or restriction formed within the hole. When in place, the guide wire 3230 may then extend from the harness tip 3434 as shown, in a proximal direction having a length sufficient to reach outside the patient's body when the balloon harness is anchored in place within the bladder. Guide wire 3230 may facilitate and improve the accuracy and efficiency of inserting a balloon catheter assembly 3500 into the bladder, and also can provide a mechanism for withdrawing the balloon harness 3430 from the bladder, down the urethra, and out of the patient. Threading a balloon catheter assembly 3500 onto the guide wire 3230 may allow for the balloon catheter assembly 3500 to be inserted into the patient and positioned substantially optimally with little guesswork. In the absence of a hole at the distal end of harness tip 3434, a guide wire 3230 may be permanently or detachably coupled to the distal end of the harness tip 3434 by, for example, providing a potted loop attachment, an adhesive connection, a stitch held within the harness tip 3434, by piercing the harness tip 3434, or by any other suitable attachment mechanism.

Examples of catheters that may serve as suitable components of a balloon catheter assembly as described herein include, but are not limited to, 18 Fr Rochester Medical catheters, Stewartville, Minn., having a silicone balloon from Polyzen, Inc., Apex, N.C. Any suitable size or configuration of catheter may be used in accordance with versions herein. The balloon catheter assembly 3500 and/or the balloon harness 3430 may be coated with a hydrophilic, lubricating, and/or anti-bacterial coating.

Figure 23:
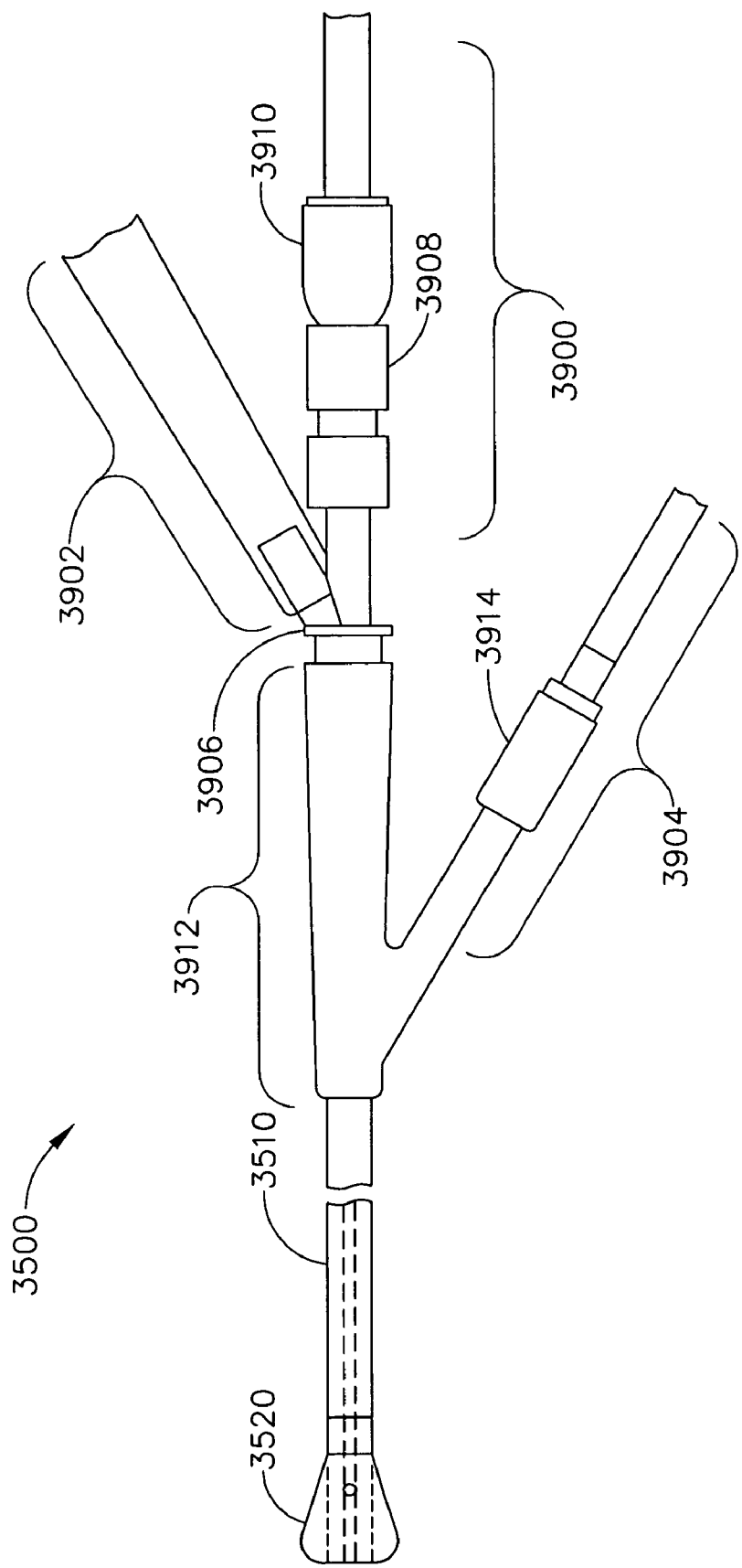
FIG. 23 is a perspective view of the proximal end of a catheter assembly having exemplary mechanisms for the pumping in of inflation fluid, the drainage of urine, and for holding a guide wire.

Referring to FIG. 23, one version of the balloon catheter assembly 3500 may include, towards the proximal end, guide wire retainer 3900, a urine removal port 3902, and an inflation port 3904. The guide wire retainer 3900 may be an assembly extending from the catheter tube 3510, through which guide wire 3230 passes. The guide wire retainer 3900, at its distal end, may be connected to a hollow plug 3906 acting as a connection to the balloon catheter assembly 3500. More proximally, the guide wire retainer 3900 may include a seal 3908 allowing for the passage of the guide wire 3230 therethrough, while preventing the passage of urine. A guide wire clamp 3910, operably configured to retain and substantially restrict the longitudinal movement of the balloon catheter assembly 3500 along the guide wire 3230, may be positioned adjacent to the seal 3908 and may be, for example, a pin vice. It will be appreciated that multiple variations of the guide wire retainer 3900 may be provided in accordance with the disclosure herein. Providing a guide wire retainer 3900, as illustrated, allows for the balloon catheter assembly 3500 to be safely held substantially in place for the duration of an anastomotic procedure.

Still referring to FIG. 23, the urine removal port 3902 may be affixed, at its distal end, at an angle to the hollow plug 3906, and may include any suitable means for removing and/or retaining urine. The hollow plug 3906, having the guide wire retainer 3900 and the urine removal port 3902 integrally attached thereto may, at its distal end, be operably configured to combine with one prong of a coupler 3912 in a friction fit. The coupler 3912 may be, for example, a polymeric Y-shaped connection member having an angled prong operably configured as the inflation port 3904. The inflation port 3904 may contain a one-way valve 3914 with a lumen therethrough, through which inflation fluid may be pumped by, for example, a syringe, or other fluid pumping means, in isolated fluid interconnection with the inflation lumen 3511, for the delivery of fluid, air, and/or gas pressure to the balloon 3520. The coupler 3912 may further include a third prong affixed to the proximal end of the catheter tube 3510 connecting the inflation port 3904, the urine removal port 3902, and the guide wire retainer 3900 to the catheter tube 3510.

Another version of the inflation port 3904 may include a two-way valve and/or a release valve mechanism incorporated with the inflation lumen that can serve to limit the fluid pressure inside the balloon by bleeding off fluid to release or limit pressure in the inflation lumen exceeding a desired amount. Providing a two-way or pressure-release valve in this manner can allow for inflation of the balloon to a known, consistent pressure limit, reducing the need for precision during inflation in actual use. The other leg of the Y-connection may be in isolated fluid communication with the main or central passage of the catheter, and used for urine drainage. It will be appreciated that multiple versions of the guide wire retainer 3900, urine removal port 3902, and/or inflation port 3904 are in accordance with the examples disclosed herein.

Referring to FIGS. 19-22, it may be desirable to have a balloon 3520 of a pear shape, at the distal portion of the catheter assembly, with the larger diameter of the shape nearest to the distal end of the assembly. This may provide for expansion of the balloon 3520 upon inflation to a larger diameter first nearer the distal end of the catheter, in the uppermost portion (with respect to the figures) of the balloon harness 3430, so as to draw itself into the bladder if was not fully inserted. Alternatively, balloon 3520 may be formed to have any other suitable shape.

Balloon 3520 may be formed from, for example, Rhodia V4000 silicone applied onto a polished DP9646-T14 mandrel, from Polyzen, Inc., Apex, N.C., by dipping into a material vat, to create a balloon skin having a pear shape. After dipping, rotation and heated air drying may be applied to control and promote a uniform skin thickness. A skin thickness of about 10 mil±0.0015 inch may be suitable. The smaller-diameter proximal end of the skin may be sized to snugly fit without substantial stretching around the selected catheter tube, which might be, for example, 14 Fr or 18 Fr, so as enable a secure bond with adhesive about the tube. The proximal end of the skin may be created by cutting around the mandrel at an appropriate location having the desired diameter corresponding to the selected catheter tube. The larger-diameter distal end of the skin may be cut around the mandrel to establish the desired length of the balloon skin. A suitable completed balloon having an inflatable length (along the longitudinal axis of the catheter) of about 0.65 inch may be constructed from a skin prepared in this manner. The balloon skin may be removed from the mandrel by injection of air. Each end of the skin may then be adhered to the catheter tube using Novagard RTV 800-306 UV/Dual Cure Class VI Paste, from the Dymax Corporation, Torrington, Conn. The balloon skin may be adhered at each of its ends to the catheter tube by a layer of adhesive applied around the tube circumference.

In versions described herein, the balloon may be sized to fit between the anchors 700 as spaced apart by the end effector assembly after driving, to fill the balloon harness 3420, and to provide adequate tissue contact area and pressure when inflated to suitable pressure. The horizontal diameter of the balloon 3520 when inflated, for example, may be about 0.75 inch, varying with the amount of inflation pressure and quantity of inflation fluid pumped thereinto. In one version, the balloon 3520 may be inflated to about 3.2 psi, to from about 3.2 to about 8.3 psi, and/or to from about 0.1 psi to about 3.2 psi. Otherwise, the manufactured diameter of the balloon when inflated to the pressure desired for the anastomosis procedure may be selected based upon the installed spacing of the anchors. As noted, the overall length of the balloon 3520 may be, for example, about 0.65 inch before inflation. Balloon 3520 manufactured as set forth herein may increase in length with the addition of inflation fluid, might reach a maximum inflation diameter (prior to bursting) of about 1.63 inches, and might sustain maximum inflation pressure prior to bursting of about 4.4 psi when unconstrained by a harness as described herein, and about 8.3 psi when constrained by a harness as described herein. Repetitive inflation and deflation may result in some loss of the balloon's pressure-sustaining capability.

Figures 19, 20:
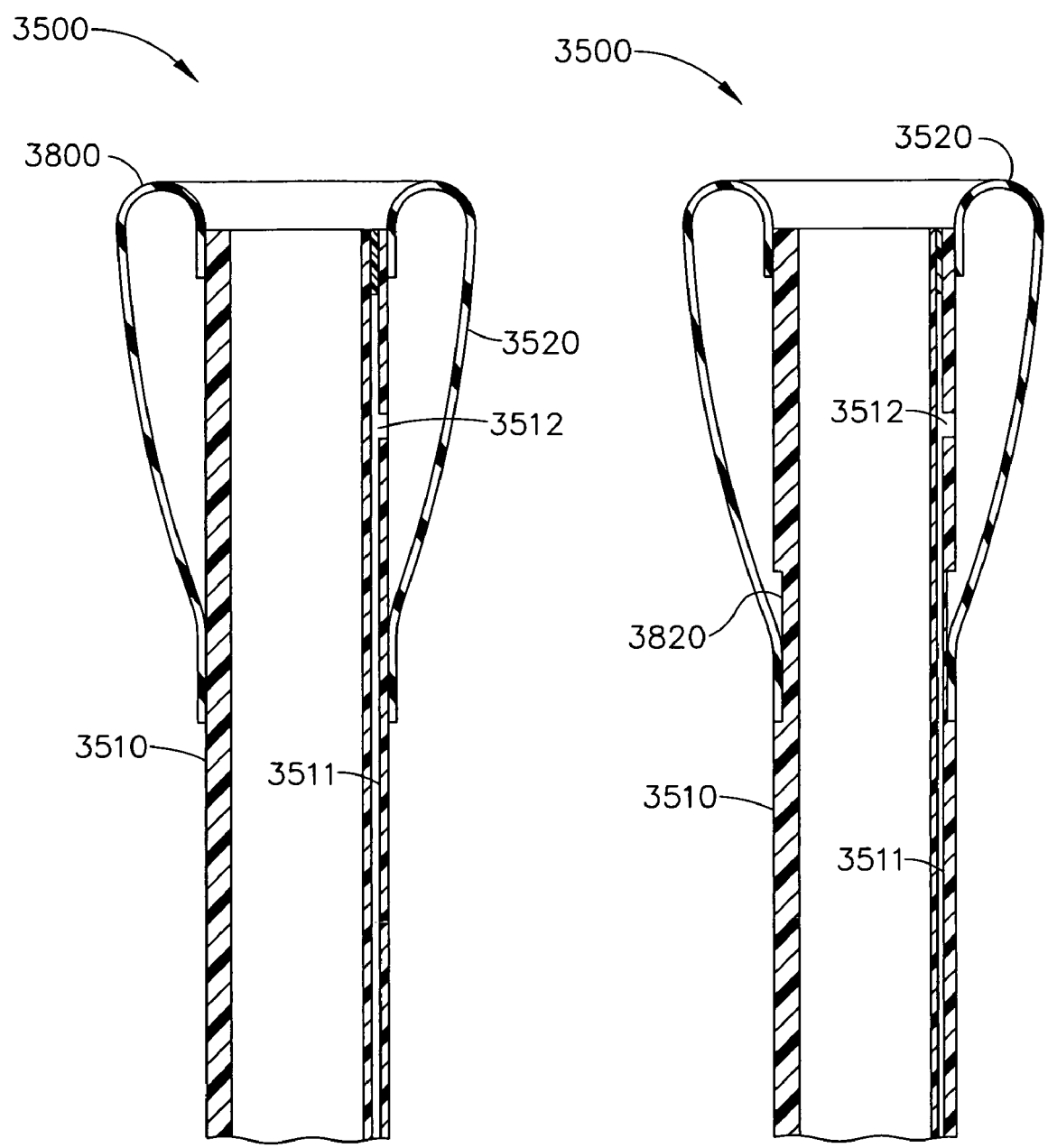
FIG. 19 is a longitudinal cross-sectional view of the distal portion of an exemplary balloon catheter assembly within the scope of the present invention.
FIG. 20 is a longitudinal cross-sectional view of the distal portion of another exemplary balloon catheter assembly within the scope of the present invention.

In FIG. 19, an example of a balloon catheter assembly 3500 is depicted having a catheter tube 3510. A version of balloon 3520 is depicted that circumferentially surrounds the catheter tube 3510 at about the distal end thereof and which may be inflated via inflation lumen 3511 and inflation port 3512. In the version shown in FIG. 19, at least a portion of the outer surface 3800 of the balloon skin has been everted and adhered to the catheter tube 3510 to form balloon 3520. Forming the balloon in this manner can reduce the number of abrupt protruding edges present at the distal end of the balloon catheter assembly that may damage, irritate, and/or interfere with the insertion of the balloon catheter assembly into, the urethra.

FIG. 20 illustrates another version of a balloon catheter assembly 3500 having a balloon 3520 that circumferentially surrounds the catheter tube 3510 at about the distal end thereof and which may be inflated via inflation lumen 3511 and inflation port 3512. In the version shown in FIG. 21, the catheter tube 3510 may be provided with a circumferential recess or step 3820 in which the proximal end of the balloon skin may be located and adhered to form balloon 3520 as shown. Providing a catheter tube with recess 3820 and adhering the balloon skin in such recess as shown in the figure can further reduce the number of abrupt protruding edges present that may damage, irritate, and/or interfere with the removal of the balloon catheter assembly into, the urethra.

Figures 21, 22:
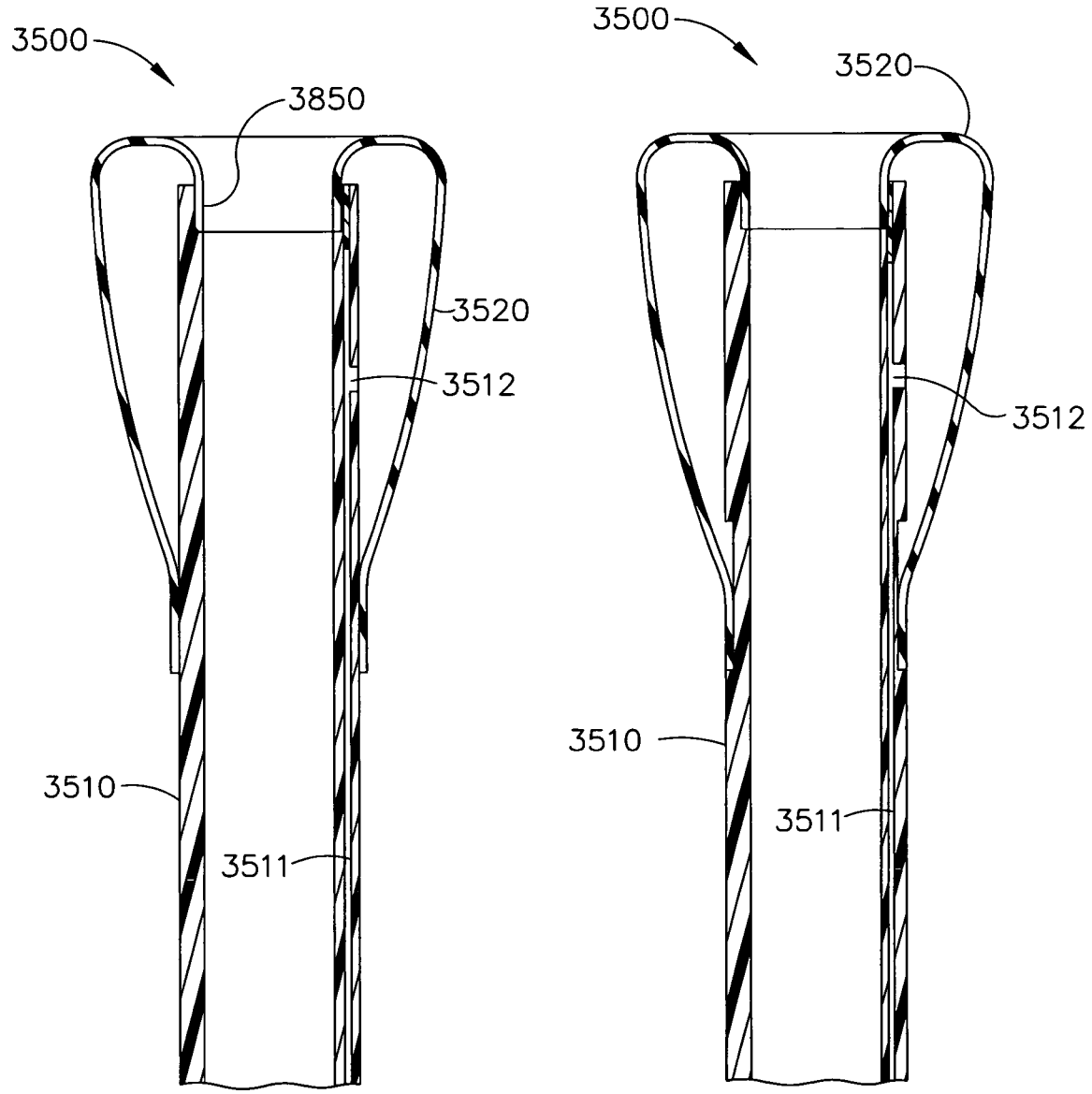
FIG. 21 is a longitudinal cross-sectional view of the distal portion of another exemplary balloon catheter assembly within the scope of the present invention.
FIG. 22 is a longitudinal cross-sectional view of the distal portion of another exemplary balloon catheter assembly within the scope of the present invention.

FIG. 21 illustrates another version of a balloon catheter assembly 3500 having a balloon 3520 that circumferentially surrounds the catheter tube 3510 at about the distal end thereof and which may be inflated via inflation lumen 3511 and inflation port 3512. In the version shown in FIG. 21, the distal end of the catheter tube 3510 may be provided with an annular recess or step 3850 into which the distal end of the balloon skin may be everted and adhered to form balloon 3520 as shown. Providing a catheter tube with recess or step 3850 and adhering the balloon skin in such recess as shown in the figure can further reduce the number of abrupt protruding edges present that may damage, irritate, and/or interfere with the removal of the balloon catheter assembly from, the urethra.

FIG. 22 illustrates another version of a balloon catheter assembly 3500 having a balloon 3520 that circumferentially surrounds the catheter tube 3510 at about the distal end thereof and which may be inflated via inflation lumen 3511 and inflation port 3512. The version of FIG. 22 illustrates a combination of the distal balloon skin attachment of FIG. 21 and the proximal balloon skin attachment of FIG. 20, which if provided, may reduce even further the number of abrupt protruding edges present that may damage, irritate, and/or interfere with the insertion and removal of the balloon catheter assembly into and from, the urethra.

Still referring to balloon 3520 as shown in FIGS. 19-22, anastomosis procedures may require leaving a balloon catheter assembly in place for about two weeks. In accordance with examples described herein, a balloon 3520 having a skin formed from a permeable or semi-permeable material may be provided, and filled with sterile water, saline solution, air, gas, or any other suitable inflation fluid, or combinations thereof. When balloon 3520 is formed from such a material, over time, balloon 3520 may, through osmosis or diffusion, change in volume and inflation pressure as a result of interaction of urine, fluid, gas, and/or air in the bladder, the inflation fluid used, and the balloon skin. This may be advantageous where, for example, the slow escape of material from the balloon into the bladder may gradually reduce the pressure within, and therefore applied by, balloon 3520, against the bladder walls 2. Reducing the pressure over time can allow for increasing of blood flow over time in the pelvic floor and bladder wall after knitting of tissues has begun. Air or other gas used as the inflation fluid may escape from the balloon more rapidly than sterile water or saline solution, and therefore, might not be suitable in some circumstances. Differences in salinity between the inflation fluid and the environment (consisting substantially of urine) will affect osmosis of water into or out of the balloon and the rate thereof. If sterile water or saline solution having lower salinity than the patient's urine is used as the inflation fluid, osmosis of water out of the balloon can occur, and the rate of osmosis might be manipulated by selecting the salinity of the inflation fluid.

It will be appreciated by those skilled in the art that the methods of manufacture, materials used, and features incorporated into the balloon and balloon harness as described herein may be varied, but that such variations are within the scope of the present invention. In particular, the objective of the versions described is to provide for a suitably matched balloon harness and balloon that can be used in combination as a means to exert suitable downward pressure against the bladder wall, urging it against the pelvic floor, in an area surrounding the openings in the bladder and urethra, whereby the balloon will be kept and constrained within the balloon harness. One objective is to cause substantially effective sealing of the bladder wall against the pelvic floor to prevent the leakage of urine into the abdominal cavity during the time required for the respective tissues to effectively knit. Another objective is to promote effective knitting of the respective tissues of the pelvic floor and the bladder wall surrounding the openings of the bladder and urethra. At the same time, it is desirable to avoid exerting excessive pressure against the tissues for extended periods of time in a manner that will unacceptably decrease circulation that helps knitting and healing, and unacceptably increase the possibility of necrosis. Utilizing techniques described herein or other suitable techniques, a balloon harness and balloon combination may be designed and manufactured that can be used to exert, for example, tissue pressures that diminish from about 100 mmHg to about 32 mmHg over the course of 48 hours. It will be appreciated that any suitable pressures and/or any suitable time durations may be utilized to adequately knit tissue.

Anchors

As described herein, anchors 700 or other suitable fasteners perform a holding function, holding the bladder wall to the pelvic floor and holding a harness to the bladder wall and/or pelvic floor. Each of the anchoring and/or fastening features discussed herein is only exemplary of a large number of designs and configurations possible within the scope of the invention.

An anchor 700 or other fastener may have one or more suitable lodging structures that function to cause the anchor to lodge in tissues after being driven thereinto, so as to resist withdrawal from the tissues. Such lodging structures may comprise barbs, circumferential ridges, projections or any other features effective to cause the anchor to lodge in the tissues when driven into them. The size, shape and number of suitable lodging structures may vary. Additionally, the inventors have determined that, whenever barbs are included on an anchor it may be desirable when manufacturing such an anchor, to round off, or radius, the protruding ends of the barbs (as viewed from the anchor forward end), in order to reduce the possibility that the barbs will snag on loose bladder wall tissue during insertion and opening of an anchor driver assembly, on which the anchor is loaded, inside the bladder.

An anchor or other fastener may also have a head or other suitable penetration-limiting structure that may function to limit the depth to which the anchor or other fastener may be driven and may also function to assist in securing proximal tissues to underlying, distal tissues. It will be appreciated that such a penetration-limiting structure need not necessarily be located at the rearward end of an anchor shaft to be effective.

It may be desirable that the forward end of an anchor be pointed or have a chisel-like shape, to facilitate more effective and/or less damaging penetration of tissues. Additionally, the inventors have determined that a point formed on the forward end of a cylindrical anchor shaft comprising three sloping flat faces in planes intersecting each other at equal angles, facilitates penetration of the anchor into tissues in a manner that minimizes the potential for the anchor to veer off-target or off-direction during driving.

When used to secure the walls of the bladder to the pelvic floor, it may be desirable for anchors to be of a length sufficient to penetrate through the bladder walls and the fascia layer of the pelvic floor. For example but not by way of limitation, such anchors are preferably about ½-inch to 2½-inches in length. For anchors that are to be installed near the rectum, it may be desirable for them to be at the shorter end of the preferred range of length.

Anchors 700 or other suitable fasteners may be formed from a substantially biocompatible polymer or metal. Where shape memory and elasticity may be desired, anchors may be manufactured using elements made of an elastic material, such as an elastic metal alloy or a thermally activated or activatable alloy, such as a nickel-titanium alloy (for example nitinol) or stainless steel alloy, so that the anchors or other fasteners may be preformed and biased with shaped ends or barbs along the shaft, which can be deployed by pushing them out of an instrument so that when they pass into the target tissue, they resume their shape within the target tissue.

If bioabsorbability is desired, anchors 700 or other suitable fasteners may be formed of a suitably substantially biocompatible and bioabsorbable material. The inventors have determined that flexible absorbable polymers (e.g., polydioxanone polymers, or polymers containing lactides, glycolides, polyglactin, etc., such as the polymers marketed by Johnson & Johnson and/or Ethicon, Inc. under the trademarks "Vicryl" and "PDS II") are potentially suitable materials. Other bioabsorbable materials having the necessary physical properties may be used.

When used to anchor harness straps for a balloon and harness system such as depicted and described herein, bioabsorbable anchors may be used to provide a bioabsorbable harness release mechanism that avoids the necessity for, or reduces the importance of, a structure or device capable of attaching a harness to, and then releasing a harness from, an anchor by mechanical means. By way of example but not of limitation, referring to FIG. 16, it can be appreciated that if a structure such as harness hook 760 on anchor 700 is bioabsorbable, with a time degradation characteristic that corresponds to the time required for the anastomosis procedure, the degradation and dissolution of harness hook 760 through bioabsorption will serve to release harness 3430 (see, e.g., FIG. 14), facilitating removal from the patient.

Additionally, there may be situations when the control of the degradation and absorption profile and/or particle breakup size of a bioabsorbable anchor or other suitable fastener may be desirable. For example, should one or more pieces of a bioabsorbable anchor, such as, for example, the head of an anchor, break away in a large piece as the anchor material is degrading after deployment, it could cause a blockage. Accordingly, bioabsorbable anchors, anchor guides, or other suitable fasteners may be designed and manufactured in a manner in which degradation rates and particle breakup size may be controlled. For example, a bioabsorbable anchor or other fastener may be formed with a cast, molded, embossed or machined-in arrangement of scoring, perforation, or grooving that creates areas of reduced thickness and increased stress of the part in selected locations, encouraging earlier fracture proximate to such areas for the purpose of reducing the size of portions that may break away as the material degrades. Alternatively, or additionally, a bioabsorbable anchor or other fastener may be formed of joined materials, or comprise joined components, having differing degradation/absorption profiles such that zones of faster and slower degradation within the part may be created, such that the possibility of breakaway and release within a body lumen of pieces that are large enough to create a possibility of blockage or other adverse effect is reduced.

In still a further embodiment, an anchor may be formed of a bimetallic or other combination of at least two materials having differing expansion properties, that will cause the part formed therefrom to take a desired shape after heating, for example, by the patient's body. In such a case, the anchor would be supplied in a cold or room-temperature state and then allowed to attain the final desired shape after installation, when heated by the patient's body.

Although nitinol may be used in this service because of its physical properties and its significant history in implantable medical devices, it may also be suitable for use as an anchor because of its overall suitability for use in conjunction with or contemplation of use of magnetic resonance imaging (MRI) technology.

An example of a method for effecting anastomosis of the bladder and urethra following a prostatectomy, as depicted and described herein, involves the driving of anchors into the pelvic floor. In such a procedure it may be desirable for anchors to be driven into the pelvic floor in locations that avoid sensitive areas and thus reduce the potential for complications. For example, referring to FIG. 18, it may be desirable to avoid driving anchors into areas proximate to the dorsal veins D of the penis, other neurovascular bundles N, the rectum R, or other sensitive anatomical features. Accordingly, referring to FIG. 18, the inventors have determined that anchors are preferably driven into the pelvic floor at locations within the zones of about 8 to about 10 o'clock, and about 2 to about 4 o'clock, about the urethra U, as shown at "A" and "B" respectively in FIG. 18. More preferably, as may be the case, for example, with use of the balloon and harness systems depicted and described herein, two anchors are driven into the pelvic floor at locations at about 9 and about 3 o'clock about the urethra, with respect to FIG. 18.

It also is important, when using an instrument of the present invention to install anchors, to avoid driving anchors into, through or across the ureteric orifices of the bladder. The exemplary embodiments of an instrument described herein facilitate avoidance of this event.

Handle

Figure 18:
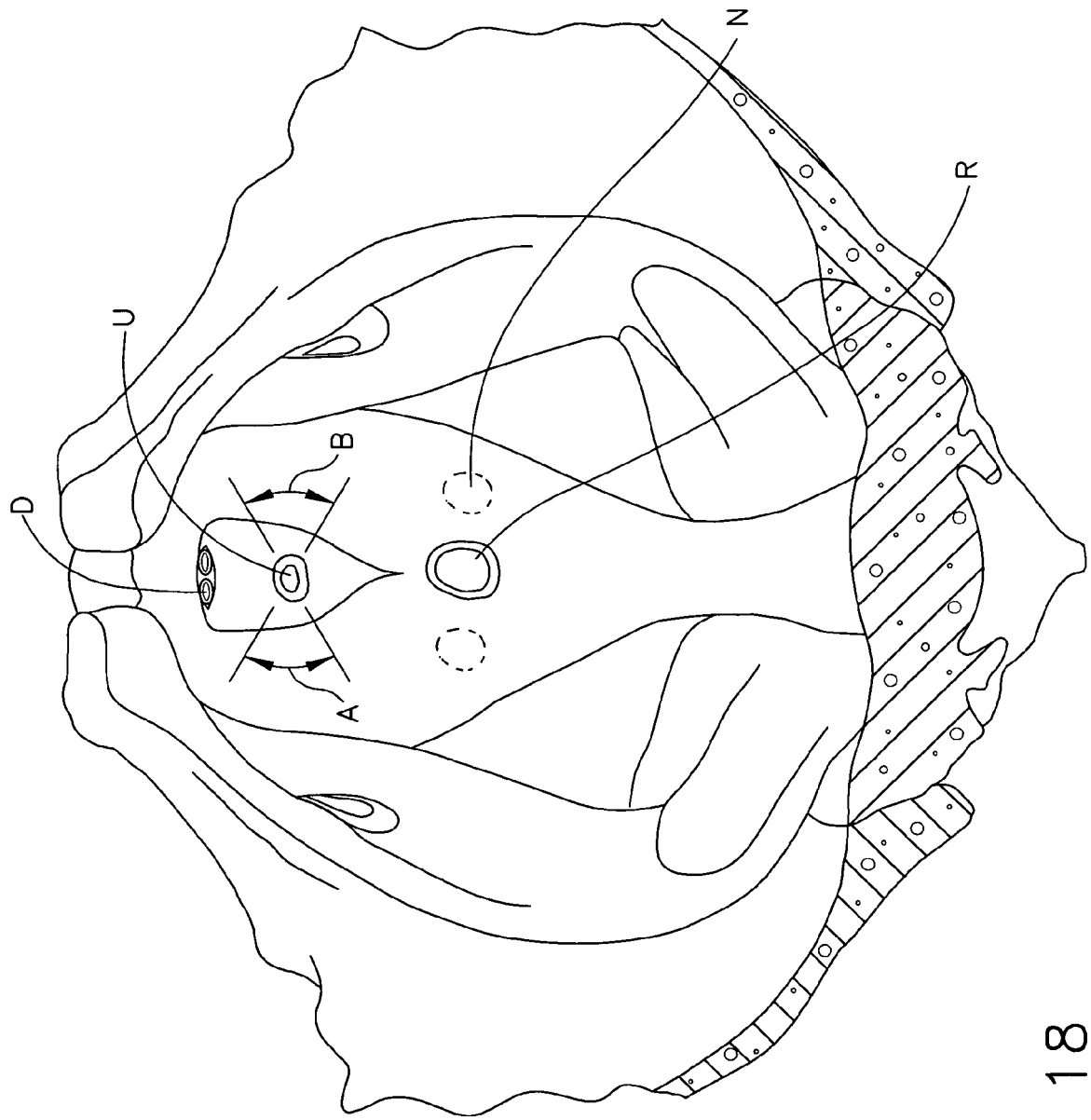
FIG. 18 is a transverse (horizontal), superior (top) partial planar view of the human male pelvis and pelvic floor architecture, depicting exemplary locations for installation of anchors in a method within the scope of the present invention.

The inventors also have developed an exemplary version of a handle assembly for the instrument that provides advantages in use of the instrument to effect the method of the present invention. Referring to FIG. 3, handle assembly 3100 may include hand support 3101 and anchor driving lever 3102 that moves about a fulcrum 3104, and have a generally ergonomic shape as shown. Anchor driving lever 3102 may be directly mechanically linked to anchor driver actuating rod or band 3261 (see FIG. 15), which in turn may be directly linked to anchor driver arms 3461 (see, e.g., FIG. 7), which can result in providing the surgeon with tactile feedback through lever 3102 concerning the driving and seating of anchors in the tissues. Referring to FIG. 3, when tube assembly 3200 includes a bend angle as shown (and as further described in pending application Ser. No. 11/096,606), hand support 3101 assists the surgeon in manipulating the instrument in a manner that utilizes the architecture of the pelvis, particularly the pubic arch, including the pubic crest, pubic tubercle, the pubic symphysis, and/or tissue associated therewith, as a fulcrum point against which the tube assembly 3200 is manipulated, to assist in drawing the end effector assembly 3400 downward (i.e., in a retrograde direction) to draw the bladder to the pelvic floor following opening of the positioner arms within the bladder and in preparation for driving anchors. Handle assembly 3100 also may be affixed in any suitable manner to tube assembly 3200 such that no relative rotation between handle assembly 3100 and tube assembly 3200 (about the longitudinal axis of tube assembly 3200) is permitted. It will also be appreciated that in this event the orientation of lever 3102 and hand support 3101 with respect to the bend angle in tube assembly 3200 enable the surgeon to easily visually determine the orientation of end effector assembly 3400 within the bladder by seeing only handle assembly 3100, enabling the surgeon to manipulate the instrument to ensure that the anchors will be driven at desirable angles and locations with respect to the urethra, such as, for example, locations "A" and "B" as depicted in FIG. 18 and as further described above. The feature of handle assembly 3100 that facilitates such easy visual determination may be in a non-uniform, or asymmetric, profile of the assembly 3100 when viewed from either side as shown in the figure. Alternatively, handle assembly 3100 may be provided with one or more markings or other visible features that serve as indicators of the orientation of the end effector assembly within the patient, the depth of the catheter, the orientation of the end effector assembly, the position of the end effector assembly, and/or the depth of the anchors after insertion into tissue.

The above-described versions of various components are examples of portions of an instrument that may be used for one or more of the steps of bringing and holding of the bladder in contact with the pelvic floor with the openings in the bladder and urethra substantially aligned, driving anchors through the bladder wall and into the pelvic floor, securing a balloon harness within the bladder lumen, inflating a balloon within the balloon harness and thereby applying pressure to the bladder wall to effect knitting of the bladder wall with the pelvic floor, and draining urine from the bladder during the time required for recovery and healing, to effect an anastomosis between the bladder and the urethra following a prostatectomy.

It will be appreciated by one skilled in the art that the components described above may have alternative configurations and embodiments useful for effecting the same steps. It will be appreciated by one skilled in the art that the components described above may, alternatively, be designed and configured so as to be useful for effecting the above-described steps in an antegrade direction rather than a retrograde direction as described above.

Thus, it can be appreciated by one skilled in the art that the mechanism comprising the positioner assembly 3440 and performing the bladder positioning function thereof may have a variety of alternative configurations including but not limited to embodiments described in pending application Ser. No. 11/094,606 (and thus including, without limitation, the positioner assembly 400, shuttlecock assembly 800 with positioner petals 830 (FIGS. 17-21), umbrella assembly 900 with reverse positioner petals 930 (FIGS. 22-27), described therein, or positioner 2017 (FIGS. 122-126), 2090 (FIGS. 110-118), 2122 (FIGS. 95, 96, 103-109) and 2168 (FIGS. 83, 84, 89-94) (all of which are described therein)), providing a transversely retractable and extendible device useful for, referring to FIG. 4, insertion in a retracted position in a retrograde direction through the urethra 5 and into bladder opening 4, extending or expanding within bladder lumen 8, catching in bladder opening 4 and manipulating to urge bladder wall 2 surrounding bladder opening 4 into contact with pelvic floor 7 surrounding urethra opening 6 with the respective openings aligned; or alternatively, insertion in a retracted position in an antegrade direction through an incision in the abdomen and an upper surface of the bladder 1, extending or expanding within bladder lumen 8, catching in bladder opening 4 and manipulating to urge bladder wall 2 surrounding bladder opening 4 into contact with pelvic floor 7 surrounding urethra opening 6 with the respective openings aligned. Generally, the positioner assembly may comprise and make use of any number of alternately extendable and retractable projections, petals, arms, claws, or other grasping or catching members for catching and gaining control of bladder wall 2 surrounding bladder opening 4. The positioner assembly may have at least one member operably connected to a longitudinal member of the instrument and alternately extendable transversely from and retractable toward the longitudinal axis thereof in response to input by a surgeon at a proximal end of the instrument. Alternatively, the instrument may be designed such that positioner arms per se may be dispensed with or otherwise have their functions as described herein be performed by other components, such as features or extensions of the anchor driver arms or other members in mechanical communication with the handle assembly.

In view of various configurations of an instrument and steps suitable for performing an anastomosis procedure as described herein, the scope of the present invention is limited only by the claims set forth below and all permissible equivalents.

We claim:

1. A method for effecting the anastomosis of a patient's bladder and pelvic floor, using an anastomotic instrument comprising a handle, a tube assembly connected to the handle, and an end effector connected to the tube assembly, wherein the handle comprises a hand support, wherein the tube assembly comprises a bend angle, wherein the end effector assembly is in operable mechanical communication with the handle via the tube assembly, the method comprising the steps of:

inserting said end effector assembly in a retrograde direction into the patient's urethra and bladder;

opening a positioner provided on said end effector assembly within the patient's bladder;

grasping said handle proximate to said hand support;

using said handle and said hand support to urge said tube assembly against the patient's pubic arch such that the pubic arch is used as a fulcrum about which said tube assembly is manipulated, where the movement of said tube assembly about said fulcrum causes said positioner to urge the patient's bladder wall towards the patient's pelvic floor; and using said handle to further actuate said anastomotic instrument.

2. The method of claim 1 wherein said bend angle is between about 80 degrees and about 90 degrees.

* * * * *